United States Patent
Kumada et al.

(10) Patent No.: US 9,850,316 B2
(45) Date of Patent: Dec. 26, 2017

(54) METHOD FOR REFOLDING ANTIBODY, PROCESS FOR PRODUCING REFOLDED ANTIBODY, REFOLDED ANTIBODY, AND USES THEREOF

(71) Applicant: NATIONAL UNIVERSITY CORPORATION KYOTO INSTITUTE OF TECHNOLOGY, Kyoto (JP)

(72) Inventors: Yoichi Kumada, Kyoto (JP); Yasuyuki Ishikawa, Kyoto (JP); Yusuke Fujiwara, Kyoto (JP); Michimasa Kishimoto, Kyoto (JP)

(73) Assignee: National University Corporation Kyoto Institute of Technology, Kyoto (JP)

( * ) Notice: Subject to any disclaimer, the term of this patent is extended or adjusted under 35 U.S.C. 154(b) by 93 days.

(21) Appl. No.: 14/767,373

(22) PCT Filed: Feb. 3, 2014

(86) PCT No.: PCT/JP2014/052475
§ 371 (c)(1),
(2) Date: Aug. 12, 2015

(87) PCT Pub. No.: WO2014/125955
PCT Pub. Date: Aug. 21, 2014

(65) Prior Publication Data
US 2015/0376297 A1 Dec. 31, 2015

(30) Foreign Application Priority Data
Feb. 15, 2013 (JP) ................................. 2013-027862

(51) Int. Cl.
| | | |
|---|---|---|
| *C07K 16/18* | (2006.01) | |
| *C07K 16/26* | (2006.01) | |
| *C07K 17/14* | (2006.01) | |
| *C07K 17/08* | (2006.01) | |
| *C07K 16/42* | (2006.01) | |
| *C07K 16/06* | (2006.01) | |
| *C07K 16/30* | (2006.01) | |
| *C07K 16/40* | (2006.01) | |
| *C08F 122/10* | (2006.01) | |

(52) U.S. Cl.
CPC ........ *C07K 16/4241* (2013.01); *C07K 16/065* (2013.01); *C07K 16/18* (2013.01); *C07K 16/26* (2013.01); *C07K 16/3007* (2013.01); *C07K 16/40* (2013.01); *C07K 17/08* (2013.01); *C08F 122/10* (2013.01); *C07K 2317/14* (2013.01); *C07K 2317/40* (2013.01); *C07K 2317/622* (2013.01); *C07K 2319/35* (2013.01)

(58) Field of Classification Search
CPC .. C07K 16/065; C07K 16/18; C07K 16/4241; C07K 16/40; C07K 16/3007; C07K 16/26; C07K 17/08; C07K 17/14; C07K 2319/35; C07K 2317/622; C07K 2317/40; C07K 2317/14; C08F 122/10
See application file for complete search history.

(56) References Cited

U.S. PATENT DOCUMENTS

| | | | |
|---|---|---|---|
| 7,662,609 B2 * | 2/2010 | Humphreys | ............. C12N 1/20 435/252.33 |
| 8,618,247 B2 | 12/2013 | Kumada et al. | |
| 2004/0091489 A1 * | 5/2004 | Pastan | ............. A61K 47/48484 424/178.1 |
| 2005/0130260 A1 | 6/2005 | Linden et al. | |
| 2010/0029911 A1 | 2/2010 | Frank et al. | |
| 2012/0309943 A1 * | 12/2012 | Kumada | ................ C07K 16/00 530/389.1 |
| 2014/0220626 A1 | 8/2014 | Kumada et al. | |

FOREIGN PATENT DOCUMENTS

| | | |
|---|---|---|
| JP | 2008-520616 A | 6/2006 |
| JP | 2007-537139 A | 12/2007 |
| JP | 2011-168505 A | 9/2011 |
| WO | 2005/03307 A1 | 4/2005 |
| WO | 2009/101807 A1 | 8/2009 |

OTHER PUBLICATIONS

Yoichi Kumada et al., "Novel solid-phase refolding method for preparation of scFv-immobilized polystyrene plates with high-antigen-binding activity", Analytical & Bioanalytical Chemistry, 2010, vol. 398, No. 3, pp. 1295-1303.
Yoichi Kumada et al., "Efficient refolding and immobilization of PMMA-tag-fused single chain Fv antibodies for sensitive immunological detection on a PMMA plate", Journal of Immunological Methods, Sep. 2014, vol. 411, pp. 1-10.
European Search Report dated Jul. 19, 2016 for European Patent Application No. 14752135.5, 11 pages.
European Search Report dated Aug. 9, 2016 for European Patent Application No. 14752135.5, 6 pages.

(Continued)

*Primary Examiner* — Phuong Huynh
(74) *Attorney, Agent, or Firm* — MH2 Technology Law Group, LLP

(57) ABSTRACT

A method for refolding an antibody, a process for producing a refolded antibody, a refolded antibody, and uses thereof are provided. A method for refolding an antibody in a liquid phase comprises the steps of denaturing an inactive antibody binding directly or through a linker to a peptide, the peptide having an isoelectric point lower than the isoelectric point of the inactive antibody, and dispersing in a liquid phase the peptide-binding inactive antibody denatured in the step above. Also provided is a process for producing a refolded antibody.

17 Claims, 13 Drawing Sheets

(56) References Cited

OTHER PUBLICATIONS

Zhang et al., "Protein aggregation during overexpression limited by peptide extensions with large net negative charge", Protein Expression & Purification, vol. 36, No. 2, Aug. 1, 2004, pp. 207-216.

Su et al., "The acidity of protein fusion partners predominantly determines the efficacy to improve the solubility of the target proteins expressed in *Escherichia coli*", Journal of Biotechnology, vol. 129, No. 3, May 1, 2007, pp. 373-382.

Yamakawa et al., "Refolding and Immobilization of Peptide-Tag-Fused VHH Antibodies and its Application to the Sensitive Immunoassays", Abstract 331405 from 2013 AIChE Annual Meeting, held Nov. 3-8, 2013 in San Francisco, CA, 1 page.

Kumada et al., "Immobilization and functional reconstitution of antibody Fab fragment by solid-phase refolding", Journal of Immunological Methods, vol. 400, Oct. 28, 2013, pp. 70-77.

\* cited by examiner

```
                            SEQUENCE LISTING

<160> NUMBER OF SEQ ID NOS: 86

<210> SEQ ID NO 1
<211> LENGTH: 16
<212> TYPE: PRT
<213> ORGANISM: Escherichia coli

<400> SEQUENCE: 1

Gly Asp Ser Asp Glu Trp Thr Phe Gly Ala Gln Met Glu Ile Trp Trp
1               5                   10                  15

<210> SEQ ID NO 2
<211> LENGTH: 20
<212> TYPE: PRT
<213> ORGANISM: Escherichia coli

<400> SEQUENCE: 2

Trp Thr Pro Ile Met Ser Thr Val Met Glu Ile Gly Tyr Asp Asn Val
1               5                   10                  15

Glu Ser Gln Arg
            20

<210> SEQ ID NO 3
<211> LENGTH: 28
<212> TYPE: PRT
<213> ORGANISM: Escherichia coli

<400> SEQUENCE: 3

Ser Asn Gly Asp Gly Val Gly Gly Ser Ile Ser Tyr Glu Tyr Glu Gly
1               5                   10                  15

Phe Gly Ile Val Gly Ala Tyr Gly Ala Ala Asp Arg
            20                  25

<210> SEQ ID NO 4
<211> LENGTH: 24
<212> TYPE: PRT
<213> ORGANISM: Escherichia coli

<400> SEQUENCE: 4

Asp Val Glu Gly Ile Gly Asp Val Asp Leu Val Asn Tyr Phe Glu Val
1               5                   10                  15

Gly Ala Thr Tyr Tyr Phe Asn Lys
            20
```

```
<210> SEQ ID NO 5
<211> LENGTH: 20
<212> TYPE: PRT
<213> ORGANISM: Escherichia coli

<400> SEQUENCE: 5

Asn Ser Asn Phe Phe Gly Leu Val Asp Gly Leu Asn Phe Ala Val Gln
1               5                   10                  15

Tyr Leu Gly Lys
            20

<210> SEQ ID NO 6
<211> LENGTH: 24
<212> TYPE: PRT
<213> ORGANISM: Escherichia coli

<400> SEQUENCE: 6

Thr Gln Asp Val Leu Leu Val Ala Gln Tyr Gln Phe Asp Phe Gly Leu
1               5                   10                  15

Arg Pro Ser Ile Ala Tyr Thr Lys
            20

<210> SEQ ID NO 7
<211> LENGTH: 24
<212> TYPE: PRT
<213> ORGANISM: Escherichia coli

<400> SEQUENCE: 7

Asn Ile Leu Ala Val Ile Val Pro Ala Leu Leu Val Ala Gly Thr Ala
1               5                   10                  15

Asn Ala Ala Glu Ile Tyr Asn Lys
            20

<210> SEQ ID NO 8
<211> LENGTH: 13
<212> TYPE: PRT
<213> ORGANISM: Escherichia coli

<400> SEQUENCE: 8

Gln Val Gly Val Pro Tyr Ile Ile Val Phe Leu Asn Lys
1               5                   10

<210> SEQ ID NO 9
<211> LENGTH: 9
<212> TYPE: PRT
<213> ORGANISM: Artificial Sequence
<220> FEATURE:
<223> OTHER INFORMATION: peptide
<220> FEATURE:
<221> NAME/KEY: variation
<222> LOCATION: 2
<223> OTHER INFORMATION: Xaa= Ile, Leu, Val, Ala, Gly, Met, Ser or Thr
<220> FEATURE:
<221> NAME/KEY: variation
<222> LOCATION: 3
<223> OTHER INFORMATION: Xaa= Ile, Leu, Val, Ala, Gly, Met, Ser or Thr
<220> FEATURE:
<221> NAME/KEY: variation
<222> LOCATION: 4
<223> OTHER INFORMATION: Xaa= Ile, Leu, Val, Ala, Gly, Met, Ser or Thr
<220> FEATURE:
<221> NAME/KEY: variation
<222> LOCATION: 7
<223> OTHER INFORMATION: Xaa= Ile, Leu, Val, Ala, Gly, Met, Ser or Thr

<400> SEQUENCE: 9

Arg Xaa Xaa Xaa Arg Arg Xaa Arg Arg
```

```
1               5

<210> SEQ ID NO 10
<211> LENGTH: 9
<212> TYPE: PRT
<213> ORGANISM: Artificial Sequence
<220> FEATURE:
<223> OTHER INFORMATION: peptide

<400> SEQUENCE: 10

Arg Ile Ile Ile Arg Arg Ile Arg Arg
1               5

<210> SEQ ID NO 11
<211> LENGTH: 9
<212> TYPE: PRT
<213> ORGANISM: Artificial Sequence
<220> FEATURE:
<223> OTHER INFORMATION: peptide

<400> SEQUENCE: 11

Arg Ala Ile Ala Arg Arg Ile Arg Arg
1               5

<210> SEQ ID NO 12
<211> LENGTH: 9
<212> TYPE: PRT
<213> ORGANISM: Artificial Sequence
<220> FEATURE:
<223> OTHER INFORMATION: peptide

<400> SEQUENCE: 12

Arg Leu Leu Leu Arg Arg Leu Arg Arg
1               5

<210> SEQ ID NO 13
<211> LENGTH: 9
<212> TYPE: PRT
<213> ORGANISM: Artificial Sequence
<220> FEATURE:
<223> OTHER INFORMATION: peptide

<400> SEQUENCE: 13

Arg Val Val Val Arg Arg Val Arg Arg
1               5

<210> SEQ ID NO 14
<211> LENGTH: 9
<212> TYPE: PRT
<213> ORGANISM: Artificial Sequence
<220> FEATURE:
<223> OTHER INFORMATION: peptide

<400> SEQUENCE: 14

Arg Ala Ala Ala Arg Arg Ala Arg Arg
1               5

<210> SEQ ID NO 15
<211> LENGTH: 9
<212> TYPE: PRT
<213> ORGANISM: Artificial Sequence
<220> FEATURE:
<223> OTHER INFORMATION: peptide

<400> SEQUENCE: 15

Arg Gly Gly Gly Arg Arg Gly Arg Arg
1               5
```

```
<210> SEQ ID NO 16
<211> LENGTH: 9
<212> TYPE: PRT
<213> ORGANISM: Artificial Sequence
<220> FEATURE:
<223> OTHER INFORMATION: peptide

<400> SEQUENCE: 16

Arg Met Met Met Arg Arg Met Arg Arg
1               5

<210> SEQ ID NO 17
<211> LENGTH: 9
<212> TYPE: PRT
<213> ORGANISM: Artificial Sequence
<220> FEATURE:
<223> OTHER INFORMATION: peptide

<400> SEQUENCE: 17

Arg Ser Ser Ser Arg Arg Ser Arg Arg
1               5

<210> SEQ ID NO 18
<211> LENGTH: 9
<212> TYPE: PRT
<213> ORGANISM: Artificial Sequence
<220> FEATURE:
<223> OTHER INFORMATION: peptide

<400> SEQUENCE: 18

Arg Thr Thr Thr Arg Arg Thr Arg Arg
1               5

<210> SEQ ID NO 19
<211> LENGTH: 12
<212> TYPE: PRT
<213> ORGANISM: Artificial Sequence
<220> FEATURE:
<223> OTHER INFORMATION: peptide

<400> SEQUENCE: 19

Lys Gly Leu Arg Gly Trp Arg Glu Met Ile Ser Leu
1               5                   10

<210> SEQ ID NO 20
<211> LENGTH: 12
<212> TYPE: PRT
<213> ORGANISM: Artificial Sequence
<220> FEATURE:
<223> OTHER INFORMATION: peptide

<400> SEQUENCE: 20

Ala Asp Tyr Leu Ser Arg Trp Gly Ser Ile Arg Asn
1               5                   10

<210> SEQ ID NO 21
<211> LENGTH: 12
<212> TYPE: PRT
<213> ORGANISM: Artificial Sequence
<220> FEATURE:
<223> OTHER INFORMATION: peptide

<400> SEQUENCE: 21

Ser Arg Val His Arg Ala Val Leu Asn Gly Val Ser
1               5                   10
```

```
<210> SEQ ID NO 22
<211> LENGTH: 12
<212> TYPE: PRT
<213> ORGANISM: Artificial Sequence
<220> FEATURE:
<223> OTHER INFORMATION: peptide

<400> SEQUENCE: 22

Arg Pro Pro Gly Val Val Arg Arg Tyr Ala Leu Gly
1               5                   10

<210> SEQ ID NO 23
<211> LENGTH: 12
<212> TYPE: PRT
<213> ORGANISM: Artificial Sequence
<220> FEATURE:
<223> OTHER INFORMATION: peptide

<400> SEQUENCE: 23

Val Arg Ser Trp Glu Glu Gln Ala Arg Val Thr Thr
1               5                   10

<210> SEQ ID NO 24
<211> LENGTH: 12
<212> TYPE: PRT
<213> ORGANISM: Artificial Sequence
<220> FEATURE:
<223> OTHER INFORMATION: peptide

<400> SEQUENCE: 24

Arg Ala Phe Ile Ala Ser Arg Arg Ile Lys Arg Pro
1               5                   10

<210> SEQ ID NO 25
<211> LENGTH: 12
<212> TYPE: PRT
<213> ORGANISM: Artificial Sequence
<220> FEATURE:
<223> OTHER INFORMATION: peptide

<400> SEQUENCE: 25

Arg Glu Ser Thr Leu Lys Gly Thr Ser Arg Ala Val
1               5                   10

<210> SEQ ID NO 26
<211> LENGTH: 12
<212> TYPE: PRT
<213> ORGANISM: Artificial Sequence
<220> FEATURE:
<223> OTHER INFORMATION: peptide

<400> SEQUENCE: 26

Ala Gly Leu Arg Leu Lys Lys Ala Ala Ile His Arg
1               5                   10

<210> SEQ ID NO 27
<211> LENGTH: 12
<212> TYPE: PRT
<213> ORGANISM: Artificial Sequence
<220> FEATURE:
<223> OTHER INFORMATION: peptide

<400> SEQUENCE: 27

Ser Ser Leu Leu Arg Ala Val Pro Glu Pro Thr Gly
1               5                   10
```

```
<210> SEQ ID NO 28
<211> LENGTH: 12
<212> TYPE: PRT
<213> ORGANISM: Artificial Sequence
<220> FEATURE:
<223> OTHER INFORMATION: peptide

<400> SEQUENCE: 28

Arg Ala Phe Ile Ala Ser Arg Arg Ile Arg Arg Pro
1               5                   10

<210> SEQ ID NO 29
<211> LENGTH: 27
<212> TYPE: PRT
<213> ORGANISM: Escherichia coli

<400> SEQUENCE: 29

Gly Gly Arg His Thr Pro Phe Phe Lys Gly Tyr Arg Pro Gln Phe Tyr
1               5                   10                  15

Phe Arg Thr Thr Asp Val Thr Gly Thr Ile Glu
            20                  25

<210> SEQ ID NO 30
<211> LENGTH: 68
<212> TYPE: PRT
<213> ORGANISM: Escherichia coli

<400> SEQUENCE: 30

Leu Leu Ser Gln Tyr Asp Phe Pro Gly Asp Asp Thr Pro Ile Val Arg
1               5                   10                  15

Gly Ser Ala Leu Lys Ala Leu Glu Gly Asp Ala Glu Trp Glu Ala Lys
            20                  25                  30

Ile Leu Glu Leu Ala Gly Phe Leu Asp Ser Tyr Ile Pro Glu Pro Glu
        35                  40                  45

Arg Ala Ile Asp Lys Pro Phe Leu Leu Pro Ile Glu Asp Val Phe Ser
    50                  55                  60

Ile Ser Gly Arg
65

<210> SEQ ID NO 31
<211> LENGTH: 78
<212> TYPE: PRT
<213> ORGANISM: Escherichia coli

<400> SEQUENCE: 31

Gly Gly Arg His Thr Pro Phe Phe Lys Gly Tyr Arg Pro Gln Phe Tyr
1               5                   10                  15

Phe Arg Thr Thr Asp Val Thr Gly Thr Ile Glu Leu Pro Glu Gly Val
            20                  25                  30

Glu Met Val Met Pro Gly Asp Asn Ile Lys Met Val Val Thr Leu Ile
        35                  40                  45

His Pro Ile Ala Met Asp Asp Gly Leu Arg Phe Ala Ile Arg Glu Gly
    50                  55                  60

Gly Arg Thr Val Gly Ala Gly Val Val Ala Lys Val Leu Ser
65                  70                  75

<210> SEQ ID NO 32
<211> LENGTH: 24
<212> TYPE: PRT
<213> ORGANISM: Escherichia coli

<400> SEQUENCE: 32
```

```
Leu Leu Ser Gln Tyr Asp Phe Pro Gly Asp Thr Pro Ile Val Arg
1               5                   10                  15

Gly Ser Ala Leu Lys Ala Leu Glu
            20
```

<210> SEQ ID NO 33
<211> LENGTH: 17
<212> TYPE: PRT
<213> ORGANISM: Escherichia coli

<400> SEQUENCE: 33

```
Ile Leu Glu Leu Ala Gly Phe Leu Asp Ser Tyr Ile Pro Glu Pro Glu
1               5                   10                  15

Arg
```

<210> SEQ ID NO 34
<211> LENGTH: 19
<212> TYPE: PRT
<213> ORGANISM: Escherichia coli

<400> SEQUENCE: 34

```
Ala Ile Asp Lys Pro Phe Leu Leu Pro Ile Glu Asp Val Phe Ser Ile
1               5                   10                  15

Ser Gly Arg
```

<210> SEQ ID NO 35
<211> LENGTH: 9
<212> TYPE: PRT
<213> ORGANISM: Escherichia coli

<400> SEQUENCE: 35

```
Gly Tyr Arg Pro Gln Phe Tyr Phe Arg
1               5
```

<210> SEQ ID NO 36
<211> LENGTH: 30
<212> TYPE: PRT
<213> ORGANISM: Escherichia coli

<400> SEQUENCE: 36

```
Met Val Met Pro Gly Asp Asn Ile Lys Met Val Val Thr Leu Ile His
1               5                   10                  15

Pro Ile Ala Met Asp Asp Gly Leu Arg Phe Ala Ile Arg Glu
            20                  25                  30
```

<210> SEQ ID NO 37
<211> LENGTH: 16
<212> TYPE: PRT
<213> ORGANISM: Escherichia coli

<400> SEQUENCE: 37

```
Met Val Val Thr Leu Ile His Pro Ile Ala Met Asp Asp Gly Leu Arg
1               5                   10                  15
```

<210> SEQ ID NO 38
<211> LENGTH: 19
<212> TYPE: PRT
<213> ORGANISM: Escherichia coli

<400> SEQUENCE: 38

```
Phe Ala Ile Arg Glu Gly Gly Arg Thr Val Gly Ala Gly Val Val Ala
1               5                   10                  15
```

Lys Val Leu

<210> SEQ ID NO 39
<211> LENGTH: 12
<212> TYPE: PRT
<213> ORGANISM: Escherichia coli

<400> SEQUENCE: 39

Thr Val Gly Ala Gly Val Ala Lys Val Leu Ser
1               5                   10

<210> SEQ ID NO 40
<211> LENGTH: 53
<212> TYPE: PRT
<213> ORGANISM: Escherichia coli

<400> SEQUENCE: 40

Leu Asn Val Pro Glu Asn Pro Ile Ile Pro Tyr Ile Glu Gly Asp Gly
1               5                   10                  15
Ile Gly Val Asp Val Thr Pro Ala Met Leu Lys Val Val Asp Ala Ala
                20                  25                  30
Val Glu Lys Ala Tyr Lys Gly Glu Arg Lys Ile Ser Trp Met Glu Ile
            35                  40                  45
Tyr Thr Gly Glu Lys
        50

<210> SEQ ID NO 41
<211> LENGTH: 58
<212> TYPE: PRT
<213> ORGANISM: Escherichia coli

<400> SEQUENCE: 41

Ala Thr His Gly Thr Ala Pro Lys Tyr Ala Gly Gln Asp Lys Val Asn
1               5                   10                  15
Pro Gly Ser Ile Ile Leu Ser Ala Glu Met Met Leu Arg His Met Gly
                20                  25                  30
Trp Thr Glu Ala Ala Asp Leu Ile Val Lys Gly Met Glu Gly Ala Ile
            35                  40                  45
Asn Ala Lys Thr Val Thr Tyr Asp Phe Glu
        50                  55

<210> SEQ ID NO 42
<211> LENGTH: 6
<212> TYPE: PRT
<213> ORGANISM: Escherichia coli

<400> SEQUENCE: 42

Asp Leu Ile Arg Glu Tyr
1               5

<210> SEQ ID NO 43
<211> LENGTH: 11
<212> TYPE: PRT
<213> ORGANISM: Escherichia coli

<400> SEQUENCE: 43

His Pro Glu Leu Thr Asp Met Val Ile Phe Arg
1               5                   10

<210> SEQ ID NO 44
<211> LENGTH: 18

```
<212> TYPE: PRT
<213> ORGANISM: Escherichia coli

<400> SEQUENCE: 44

Leu Ile Asp Gly Gly Pro Trp Leu Lys Val Lys Asn Pro Asn Thr Gly
1               5                   10                  15

Lys Glu

<210> SEQ ID NO 45
<211> LENGTH: 20
<212> TYPE: PRT
<213> ORGANISM: Escherichia coli

<400> SEQUENCE: 45

Leu Asn Val Pro Glu Asn Pro Ile Ile Pro Tyr Ile Glu Gly Asp Gly
1               5                   10                  15

Ile Gly Val Asp
            20

<210> SEQ ID NO 46
<211> LENGTH: 27
<212> TYPE: PRT
<213> ORGANISM: Escherichia coli

<400> SEQUENCE: 46

Leu Asn Val Pro Glu Asn Pro Ile Ile Pro Tyr Ile Glu Gly Asp Gly
1               5                   10                  15

Ile Gly Val Asp Val Thr Pro Ala Met Leu Lys
            20                  25

<210> SEQ ID NO 47
<211> LENGTH: 12
<212> TYPE: PRT
<213> ORGANISM: Escherichia coli

<400> SEQUENCE: 47

Lys Ile Ser Trp Met Glu Ile Tyr Thr Gly Glu Lys
1               5                   10

<210> SEQ ID NO 48
<211> LENGTH: 25
<212> TYPE: PRT
<213> ORGANISM: Escherichia coli

<400> SEQUENCE: 48

Ala Thr His Gly Thr Ala Pro Lys Tyr Ala Gly Gln Asp Lys Val Asn
1               5                   10                  15

Pro Gly Ser Ile Ile Leu Ser Ala Glu
            20                  25

<210> SEQ ID NO 49
<211> LENGTH: 21
<212> TYPE: PRT
<213> ORGANISM: Escherichia coli

<400> SEQUENCE: 49

Val Asn Pro Gly Ser Ile Ile Leu Ser Ala Glu Met Met Leu Arg His
1               5                   10                  15

Met Gly Trp Thr Glu
            20

<210> SEQ ID NO 50
```

```
<211> LENGTH: 32
<212> TYPE: PRT
<213> ORGANISM: Escherichia coli

<400> SEQUENCE: 50

Met Leu Arg His Met Gly Trp Thr Glu Ala Ala Asp Leu Ile Val Lys
1               5                   10                  15

Gly Met Glu Gly Ala Ile Asn Ala Lys Thr Val Thr Tyr Asp Phe Glu
            20                  25                  30

<210> SEQ ID NO 51
<211> LENGTH: 13
<212> TYPE: PRT
<213> ORGANISM: Escherichia coli

<400> SEQUENCE: 51

His Met Gly Trp Thr Glu Ala Ala Asp Leu Ile Val Lys
1               5                   10

<210> SEQ ID NO 52
<211> LENGTH: 15
<212> TYPE: PRT
<213> ORGANISM: Escherichia coli

<400> SEQUENCE: 52

Val Asn Pro Gly Ser Ile Ile Leu Ser Ala Glu Met Met Leu Arg
1               5                   10                  15

<210> SEQ ID NO 53
<211> LENGTH: 48
<212> TYPE: DNA
<213> ORGANISM: Escherichia coli

<400> SEQUENCE: 53
ggcgacagcg acgagtggac cttcggtgcc cagatggaaa tctggtgg            48

<210> SEQ ID NO 54
<211> LENGTH: 60
<212> TYPE: DNA
<213> ORGANISM: Escherichia coli

<400> SEQUENCE: 54
tggacgccaa tcatgagcac cgtgatggaa atcggctacg acaacgtcga atcccagcgc   60

<210> SEQ ID NO 55
<211> LENGTH: 84
<212> TYPE: DNA
<213> ORGANISM: Escherichia coli

<400> SEQUENCE: 55
tctaacggcg acggtgttgg cggttctatc agctacgaat acgaaggctt tggtatcgtt   60
ggtgcttatg gtgcagctga ccgt                                          84

<210> SEQ ID NO 56
<211> LENGTH: 72
<212> TYPE: DNA
<213> ORGANISM: Escherichia coli

<400> SEQUENCE: 56
gacgtagaag gtatcggtga tgttgatctg gtgaactact ttgaagtggg tgcaacctac   60
tacttcaaca aa                                                       72
```

```
<210> SEQ ID NO 57
<211> LENGTH: 60
<212> TYPE: DNA
<213> ORGANISM: Escherichia coli

<400> SEQUENCE: 57
aactccaact tctttggtct ggttgatggc ctgaacttcg ctgttcagta cctgggtaaa    60

<210> SEQ ID NO 58
<211> LENGTH: 72
<212> TYPE: DNA
<213> ORGANISM: Escherichia coli

<400> SEQUENCE: 58
acgcaagacg ttctgttagt tgcgcaatac cagttcgatt tcggtctgcg tccgtccatc    60
gcttacacca aa                                                        72

<210> SEQ ID NO 59
<211> LENGTH: 72
<212> TYPE: DNA
<213> ORGANISM: Escherichia coli

<400> SEQUENCE: 59
aatattctgg cagtgatcgt ccctgctctg ttagtagcag gtactgcaaa cgctgcagaa    60
atctataaca aa                                                        72

<210> SEQ ID NO 60
<211> LENGTH: 39
<212> TYPE: DNA
<213> ORGANISM: Escherichia coli

<400> SEQUENCE: 60
caggtaggcg ttccgtacat catcgtgttc ctgaacaaa                           39

<210> SEQ ID NO 61
<211> LENGTH: 27
<212> TYPE: DNA
<213> ORGANISM: Artificial Sequence
<220> FEATURE:
<223> OTHER INFORMATION: synthetic DNA 10

<400> SEQUENCE: 61
cgtatcatca tccgaaggat tcgacga                                        27

<210> SEQ ID NO 62
<211> LENGTH: 27
<212> TYPE: DNA
<213> ORGANISM: Artificial Sequence
<220> FEATURE:
<223> OTHER INFORMATION: synthetic DNA 11

<400> SEQUENCE: 62
cgtgcgattg cgcgaaggat tcgacga                                        27

<210> SEQ ID NO 63
<211> LENGTH: 81
<212> TYPE: DNA
<213> ORGANISM: Escherichia coli

<400> SEQUENCE: 63
ggcggccgtc atactccgtt cttcaaaggc taccgtccgc agttctactt ccgtactact    60
gacgtgactg gtaccatcga a                                              81
```

```
<210> SEQ ID NO 64
<211> LENGTH: 204
<212> TYPE: DNA
<213> ORGANISM: Escherichia coli

<400> SEQUENCE: 64
cttctgtctc agtacgactt cccgggcgac gacactccga tcgttcgtgg ttctgctctg      60
aaagcgctgg aaggcgacgc agagtgggaa gcgaaaatcc tggaactggc tggcttcctg     120
gattcttaca ttccggaacc agagcgtgcg attgacaagc cgttcctgct gccgatcgaa     180
gacgtattct ccatctccgg tcgt                                            204

<210> SEQ ID NO 65
<211> LENGTH: 234
<212> TYPE: DNA
<213> ORGANISM: Escherichia coli

<400> SEQUENCE: 65
ggcggccgtc atactccgtt cttcaaaggc taccgtccgc agttctactt ccgtactact      60
gacgtgactg gtaccatcga actgccggaa ggcgtagaga tggtaatgcc gggcgacaac     120
atcaaaatgg ttgttaccct gatccacccg atcgcgatgg acgacggtct gcgtttcgca     180
atccgtgaag cggccgtac cgttggcgcg ggcgttgtag caaaagttct gagc            234

<210> SEQ ID NO 66
<211> LENGTH: 72
<212> TYPE: DNA
<213> ORGANISM: Escherichia coli

<400> SEQUENCE: 66
cttctgtctc agtacgactt cccgggcgac gacactccga tcgttcgtgg ttctgctctg      60
aaagcgctgg aa                                                          72

<210> SEQ ID NO 67
<211> LENGTH: 51
<212> TYPE: DNA
<213> ORGANISM: Escherichia coli

<400> SEQUENCE: 67
atcctggaac tggctggctt cctggattct tacattccgg aaccagagcg t               51

<210> SEQ ID NO 68
<211> LENGTH: 57
<212> TYPE: DNA
<213> ORGANISM: Escherichia coli

<400> SEQUENCE: 68
gcgattgaca agccgttcct gctgccgatc gaagacgtat tctccatctc cggtcgt         57

<210> SEQ ID NO 69
<211> LENGTH: 27
<212> TYPE: DNA
<213> ORGANISM: Escherichia coli

<400> SEQUENCE: 69
ggctaccgtc cgcagttcta cttccgt                                          27

<210> SEQ ID NO 70
<211> LENGTH: 90
<212> TYPE: DNA
<213> ORGANISM: Escherichia coli
```

<400> SEQUENCE: 70
atggtaatgc cgggcgacaa catcaaaatg gttgttaccc tgatccaccc gatcgcgatg    60
gacgacggtc tgcgtttcgc aatccgtgaa                                     90

<210> SEQ ID NO 71
<211> LENGTH: 48
<212> TYPE: DNA
<213> ORGANISM: Escherichia coli

<400> SEQUENCE: 71
atggttgtta ccctgatcca cccgatcgcg atggacgacg gtctgcgt                 48

<210> SEQ ID NO 72
<211> LENGTH: 57
<212> TYPE: DNA
<213> ORGANISM: Escherichia coli

<400> SEQUENCE: 72
ttcgcaatcc gtgaaggcgg ccgtaccgtt ggcgcgggcg ttgtagcaaa agttctg       57

<210> SEQ ID NO 73
<211> LENGTH: 36
<212> TYPE: DNA
<213> ORGANISM: Escherichia coli

<400> SEQUENCE: 73
accgttggcg cgggcgttgt agcaaaagtt ctgagc                              36

<210> SEQ ID NO 74
<211> LENGTH: 159
<212> TYPE: DNA
<213> ORGANISM: Escherichia coli

<400> SEQUENCE: 74
ctcaacgttc ctgaaaatcc gattatccct tacattgaag gtgatggaat cggtgtagat    60
gtaaccccag ccatgctgaa agtggtcgac gctgcagtcg agaaagccta taaggcgag    120 cgtaaaatct cctggatgga aatttacacc ggtgaaaaa                          159

<210> SEQ ID NO 75
<211> LENGTH: 174
<212> TYPE: DNA
<213> ORGANISM: Escherichia coli

<400> SEQUENCE: 75
gccacccacg gtactgcgcc gaaatatgcc ggtcaggaca agtaaatcc tggctctatt    60 attctctccg ctgagatgat gctgcgccac atgggttgga ccgaagcggc tgacttaatt   120
gttaaaggta tggaaggcgc aatcaacgcg aaaaccgtaa cctatgactt cgag         174

<210> SEQ ID NO 76
<211> LENGTH: 18
<212> TYPE: DNA
<213> ORGANISM: Escherichia coli

<400> SEQUENCE: 76
gatctgattc gtgaatat                                                  18

<210> SEQ ID NO 77
<211> LENGTH: 33
<212> TYPE: DNA

<213> ORGANISM: Escherichia coli

<400> SEQUENCE: 77
caccctgaac tgaccgatat ggttatcttc cgt    33

<210> SEQ ID NO 78
<211> LENGTH: 54
<212> TYPE: DNA
<213> ORGANISM: Escherichia coli

<400> SEQUENCE: 78
ctgatcgacg gtggcccgtg gctgaaagtt aaaaacccga acactggcaa agag    54

<210> SEQ ID NO 79
<211> LENGTH: 60
<212> TYPE: DNA
<213> ORGANISM: Escherichia coli

<400> SEQUENCE: 79
ctcaacgttc ctgaaaatcc gattatccct tacattgaag gtgatggaat cggtgtagat    60

<210> SEQ ID NO 80
<211> LENGTH: 81
<212> TYPE: DNA
<213> ORGANISM: Escherichia coli

<400> SEQUENCE: 80
ctcaacgttc ctgaaaatcc gattatccct tacattgaag gtgatggaat cggtgtagat    60
gtaaccccag ccatgctgaa a    81

<210> SEQ ID NO 81
<211> LENGTH: 36
<212> TYPE: DNA
<213> ORGANISM: Escherichia coli

<400> SEQUENCE: 81
aaaatctcct ggatggaaat ttacaccggt gaaaaa    36

<210> SEQ ID NO 82
<211> LENGTH: 75
<212> TYPE: DNA
<213> ORGANISM: Escherichia coli

<400> SEQUENCE: 82
gccacccacg gtactgcgcc gaaatatgcc ggtcaggaca agtaaatcc tggctctatt    60 attctctccg ctgag    75

<210> SEQ ID NO 83
<211> LENGTH: 63
<212> TYPE: DNA
<213> ORGANISM: Escherichia coli

<400> SEQUENCE: 83
gtaaatcctg gctctattat tctctccgct gagatgatgc tgcgccacat gggttggacc    60
gaa    63

<210> SEQ ID NO 84
<211> LENGTH: 96
<212> TYPE: DNA
<213> ORGANISM: Escherichia coli

<400> SEQUENCE: 84

```
atgctgcgcc acatggggttg gaccgaagcg gctgacttaa ttgttaaagg tatggaaggc    60
gcaatcaacg cgaaaaccgt aacctatgac ttcgag                               96

<210> SEQ ID NO 85
<211> LENGTH: 39
<212> TYPE: DNA
<213> ORGANISM: Escherichia coli

<400> SEQUENCE: 85
cacatgggtt ggaccgaagc ggctgactta attgttaaa                            39

<210> SEQ ID NO 86
<211> LENGTH: 45
<212> TYPE: DNA
<213> ORGANISM: Escherichia coli

<400> SEQUENCE: 86
gtaaatcctg gctctattat tctctccgct gagatgatgc tgcgc                     45
```

METHOD FOR REFOLDING ANTIBODY, PROCESS FOR PRODUCING REFOLDED ANTIBODY, REFOLDED ANTIBODY, AND USES THEREOF

CROSS-REFERENCE TO RELATED APPLICATIONS

This application is a U.S. National Stage application of PCT/JP2014/052475 filed 3 Feb. 2014, which claims priority to Japanese Application No. 2013-027862 filed 15 Feb. 2013, the entire disclosures of which are hereby incorporated by reference in their entireties.

TECHNICAL FIELD

The present invention relates to a method for refolding an antibody, a process for producing a refolded antibody, a refolded antibody, and uses thereof.

BACKGROUND ART

Antibodies have been widely used in various fields including biotechnology, pharmaceuticals, and foods. Each antibody has its own activity. Based on their activity, antibodies are selected for use for different purposes. Various methods are known for producing antibodies, and mass production of desired antibodies is also possible.

However, known production methods do not always produce antibodies with sufficient activity. For example, most antibodies are often inactive when produced with the use of recombinant *Escherichia coli* or the like as a host. To obtain antibodies with desired activity, a refolding operation must further be performed with respect to the obtained inactive antibodies.

In relation to refolding, a method for refolding a denatured protein has been reported, comprising adding a denatured protein dropwise to a refolding buffer containing, for example, arginine, reduced glutathione, and oxidized glutathione (Patent Literature (PTL) 1). A method comprising the step of refolding a membrane protein in the presence of a surfactant has also been reported (Patent Literature (PTL) 2). There is also a report stating that after a peptide having an anchoring part that binds to an activated solid phase was allowed to adsorb onto the solid-phase surface by chelate bonding, wherein the activated solid phase contains metal ions that are coordinatively bound to metal-chelating ligands, refolding of this peptide was successfully performed on the solid-phase surface (Patent Literature (PTL) 3). There is also a report stating that after a specific peptide was allowed to adsorb onto a solid-phase surface, the steric structure of the peptide was successfully reconstructed on the solid-phase surface (Patent Literature (PTL) 4 and Patent Literature (PTL) 5).

As described above, various refolding methods have thus far been reported. However, the refolding efficiency is low in these known methods.

CITATION LIST

Patent Literature

PTL 1: WO 2005/033307
PTL 2: JP2007-537139A
PTL 3: JP2008-520616A
PTL 4: WO 2009/101807
PTL 5: JP2011-168505

SUMMARY OF INVENTION

Technical Problem

In view of the above, an object of the present invention is to provide a means capable of more efficiently performing refolding of an antibody having desired activity. More specifically, an object of the present invention is to provide a method for refolding an antibody in a liquid phase, the method capable of more efficiently refolding a desired antibody. Another object of the present invention is to provide a process for efficiently producing a refolded antibody in a liquid phase, and to provide a refolded antibody obtainable by this process. A further object of the present invention is to provide a method for immobilizing on a substrate an antibody refolded by the above method, and to provide a substrate on which a refolded antibody is immobilized by this method. A still further object of the present invention is to provide a composition for refolding an antibody in a liquid phase, an auxiliary agent for refolding an antibody in a liquid phase, a peptide expression vector for refolding an antibody in a liquid phase, a peptide-binding-antibody expression vector for refolding an antibody in a liquid phase, a transformant obtained using this vector, a peptide-binding antibody obtained from this transformant, and the like.

Solution to Problem

The present inventors conducted extensive research to achieve the above objects and found that refolding of a denatured inactive antibody in a liquid phase is efficiently performed by using a peptide having an isoelectric point lower than the isoelectric point of the inactive antibody, and that efficient production of desired antibodies is thus achieved. The present inventors have conducted further research based on these findings, and thereby accomplished the present invention.

More specifically, the present invention provides the following:

Item 1. A method for refolding an antibody in a liquid phase, the method comprising the steps of:
(1-1) denaturing an inactive antibody binding directly or through a linker to a peptide, the peptide having an isoelectric point lower than the isoelectric point of the inactive antibody; and
(1-2) dispersing in a liquid phase the peptide-binding inactive antibody denatured in step (1-1) above.

Item 2. The refolding method according to Item 1, wherein the antibody is at least one member selected from the group consisting of single-chain antibodies, Fab fragments, F(ab')2 fragments, single-domain antibodies, multivalent single-chain antibodies, single-chain antibodies fused with a constant region, and full-length antibodies.

Item 3. The refolding method according to Item 1 or 2, wherein the isoelectric point of the peptide is 8.5 or lower.

Item 4. The refolding method according to any one of Items 1 to 3, wherein the peptide has an affinity for a substrate.

Item 5. The refolding method according to any one of Items 1 to 4, wherein the linker is a peptide having an affinity for a substrate.

Item 6. A process for producing a refolded antibody, the process comprising the steps of:

(2-1) denaturing an inactive antibody binding directly or through a linker to a peptide, the peptide having an isoelectric point lower than the isoelectric point of the inactive antibody; and (2-2) dispersing in a liquid phase the peptide-binding inactive antibody denatured in step (2-1) above.

Item 7. The production process according to Item 6, wherein the antibody is at least one member selected from the group consisting of single-chain antibodies, Fab fragments, F(ab')2 fragments, single-domain antibodies, multivalent single-chain antibodies, single-chain antibodies fused with a constant region, and full-length antibodies.

Item 8. The production process according to Item 6 or 7, wherein the isoelectric point of the peptide is 8.5 or lower.

Item 9. The production process according to any one of Items 6 to 8, wherein the peptide has an affinity for a substrate.

Item 10. The production process according to any one of Items 6 to 9, wherein the linker is a peptide having an affinity for a substrate.

Item 11. A refolded antibody obtained by the production process of any one of Items 6 to 10.

Item 12. An auxiliary agent for refolding an antibody in a liquid phase, the auxiliary agent consisting of the peptide described in any one of Items 1, 3, 4, 6, 8, and 9 having an isoelectric point lower than the isoelectric point of an inactive antibody.

Item 13. A method for immobilizing a refolded antibody on a substrate, the method comprising the step of bringing an antibody refolded by the method of any one of Items 1 to 5 and/or a refolded antibody obtained by the production process of any one of Items 6 to 10 into contact with a substrate.

Item 14. The immobilizing method according to Item 13, wherein the antibody is immobilized on the substrate via a peptide binding to the antibody.

Item 15. The immobilizing method according to Item 13 or 14, wherein the peptide having an isoelectric point lower than the isoelectric point of the inactive antibody is a peptide (a) or (b) below, and wherein the substrate is at least one member selected from the group consisting of polycarbonate and polymethyl methacrylate:

(a) a peptide having the amino acid sequence represented by any one of SEQ ID NOs: 1 to 4; or (b) a peptide having an amino acid sequence in which one or a plurality of the amino acids are deleted, substituted, and/or added in the amino acid sequence of (a), and having an affinity for at least one member selected from the group consisting of polycarbonate and polymethyl methacrylate.

Item 16. A substrate on which a refolded antibody is immobilized by the immobilizing method of any one of Items 13 to 15.

Item 17. A composition for refolding an antibody in a liquid phase, the composition comprising an inactive antibody binding directly or through a linker to a peptide, the peptide having an isoelectric point lower than the isoelectric point of the inactive antibody.

Item 18. The composition according to Item 17, further comprising a solution having a pH higher than by 0.5 or more the isoelectric point of the inactive antibody binding directly or through a linker to the peptide.

Item 19. A peptide-binding-antibody expression vector for refolding an antibody in a liquid phase, the vector comprising a polynucleotide encoding an antibody and a polynucleotide encoding a peptide having an isoelectric point lower than the isoelectric point of the antibody, these polynucleotides being linked to each other directly or through a linker.

Item 20. A transformant obtained by transforming a host cell by introducing the vector of Item 19 into the host cell.

Item 21. An antibody binding to a peptide, the antibody obtained from the transformant of Item 20.

Item 22. A peptide expression vector for refolding an antibody in a liquid phase, the vector comprising a polynucleotide encoding the peptide described in any one of Items 1, 3, 4, 6, 8, and 9 having an isoelectric point lower than the isoelectric point of the inactive antibody.

Item 23. An antibody binding directly or through a linker to a peptide consisting of an aspartyl residue, the peptide having an isoelectric point lower than the isoelectric point of the inactive antibody.

Item 24. The antibody according to Item 23, which is an inactive antibody or a refolded antibody.

Advantageous Effects of Invention

According to the present invention, an inactive antibody is efficiently refolded to have desired activity. In the present invention, an antibody having desired activity is efficiently obtained, making it possible to reduce the cost for producing antibodies, and thus to provide less expensive antibodies.

The present invention uses a peptide having an isoelectric point lower than the isoelectric point of an inactive antibody. When this peptide has an ability to adsorb onto a substrate, it is possible for an antibody having desired activity obtained by refolding to be immobilized on the substrate via this peptide in an easier, highly efficient, and highly dense manner, while maintaining the activity and while further controlling its orientation to be more uniform.

In addition to the peptide having an isoelectric point lower than the isoelectric point of the inactive antibody, the antibody targeted by the present invention may further bind to a different peptide having an ability to adsorb onto a substrate. Therefore, even when the peptide having an isoelectric point lower than the isoelectric point of the inactive antibody does not have an ability to adsorb onto a substrate, it is possible for an antibody having desired activity obtained by refolding to be immobilized on the substrate via the different peptide having an ability to adsorb onto the substrate in an easier, highly efficient, and highly dense manner, while maintaining the activity and while further controlling its orientation to be more uniform.

In view of the above, the present invention makes it possible to efficiently obtain an antibody having desired activity, and easily and efficiently obtain a highly precise substrate on which an antibody having desired activity is immobilized. Accordingly, the present invention contributes to further wide use of technology for using antibodies in various fields including biotechnology, pharmaceuticals, and foods.

DESCRIPTION OF EMBODIMENTS

Figure 1:
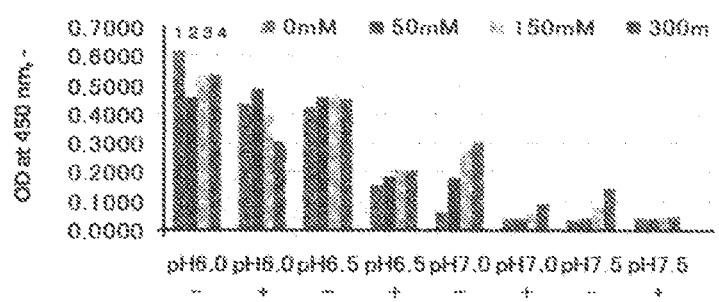
FIG. 1 is graphs showing the results of refolding of an anti-CEA antibody.
Figure 1:
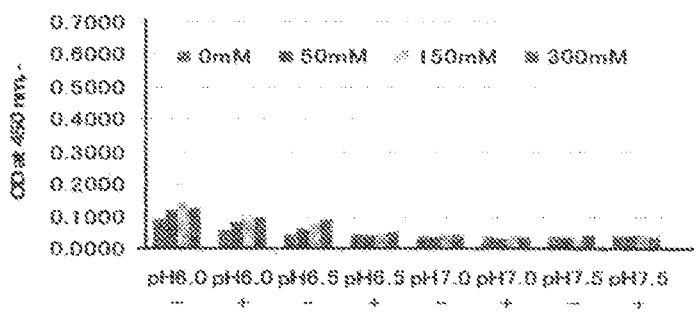

The following describes the present invention.
1. Method for Refolding an Antibody in a Liquid Phase The method for refolding an antibody in a liquid phase of the present invention comprises the steps of:
(1-1) denaturing an inactive antibody binding directly or through a linker to a peptide; and
(1-2) dispersing in a liquid phase the peptide-binding inactive antibody denatured in step (1-1) above.
In step (1-1) above, the peptide has an isoelectric point lower than the isoelectric point of the inactive antibody.

As described above, step (1-1) according to the present invention is for denaturing an inactive antibody binding directly or through a linker to a peptide.

The antibody as used herein is not limited, and may be any antibody. Examples thereof include single-chain antibodies, Fab fragments, F(ab')2 fragments, single-domain antibodies (e.g., nanobodies, and variable domain of heavy chain of heavy-chain antibody (VHH)), multivalent single-chain antibodies, single-chain antibodies fused with a constant region, full-length antibodies (including inclonals), and the like.

The peptide used in step (1-1), i.e., the peptide having an isoelectric point (pI) lower than the isoelectric point of the inactive antibody, has an isoelectric point lower than the isoelectric point of the inactive antibody. The isoelectric point of the peptide is not limited, as long as it is lower than the isoelectric point of the inactive antibody. For example, the peptide preferably has an isoelectric point of 8.5 or lower, more preferably 8 or lower, still more preferably 7.5 or lower, and further particularly preferably 7 or lower.

The peptide is not limited as long as the description above is satisfied. The peptide preferably comprises, for example, 5 to 50 amino acid residues, more preferably 5 to 41 amino acid residues, and still more preferably 10 to 31 amino acid residues.

The peptide having the above-mentioned isoelectric point and comprising the above-mentioned number of amino acid residues preferably comprises, for example, 2 or more, more preferably 3 to 20, and even more preferably 4 to 15 acidic amino acid residues.

The peptide comprising the above-mentioned number of acidic amino acid residues is preferably, for example, a peptide in which the number of acidic amino acid residues is more than that of basic amino acid residues. For example, the peptide is more preferably such that the number of acidic amino acid residues is more than that of basic amino acid residues by one or more, still more preferably 2 to 25, and particularly preferably 4 to 20.

The acidic amino acids as used herein represent aspartic acid and glutamic acid, and the basic amino acids represent lysine, arginine, and histidine.

For example, the peptide preferably enables the isoelectric point of the entire "inactive antibody binding directly to the peptide" to be lower than the isoelectric point of "the inactive antibody" alone by 0.3 or more, more preferably about 0.3 to 5, and even more preferably about 0.3 to 4. Further, for example, the peptide preferably enables the isoelectric point of the entire "inactive antibody binding through a linker to the peptide" to be lower than the isoelectric point of "the inactive antibody" alone by 0.3 or more, more preferably about 0.3 to 5, and even more preferably about 0.3 to 4.

Although it depends on the isoelectric point of the antibody, the peptide is preferably capable of enabling the isoelectric point of the entire "inactive antibody binding directly or through a linker to the peptide" to be, for example, about 3.5 to 7.5, more preferably about 3.5 to 7, and even more preferably about 4 to 6.5.

The peptide having an isoelectric point lower than the isoelectric point of the inactive antibody used in the present invention is selected in consideration of the isoelectric point of the inactive antibody to which the peptide is linked. A person skilled in the art can easily select the inactive antibody and the peptide to be used. The isoelectric point as used in the present invention is a value calculated by using the commercially available software Genetyx ver. 6 (produced by Genetyx Corporation). When an amino acid sequence is input following the procedure of the software, the isoelectric point is calculated by the program based on the sequence of the amino acid residues. For example, in the present invention, if antibodies have the same amino acid sequence, the isoelectric points of these antibodies are calculated to be identical, regardless of their activeness and inactiveness. That is, in the present invention, an "inactive antibody" and an "antibody" have the same isoelectric point.

The peptide is not limited as long as it has an isoelectric point lower than the isoelectric point of the inactive antibody, as described above. Examples thereof include a peptide consisting of aspartic acid and/or glutamic acid residues; a peptide having aspartic acid and/or glutamic acid residues more than basic amino acids residues; a peptide having the amino acid sequence of any one of SEQ ID NOs: 1 to 4; a peptide having two or more amino acid sequences of any of SEQ ID NOs: 1 to 4; a peptide having an amino acid sequence in which one or a plurality of the amino acids are deleted, substituted, and/or added in the amino acid sequence of these peptides; and the like.

The peptide of the present invention includes oligopeptides, polypeptides, and proteins, which are named accordingly depending on the number of amino acid residues. In the peptide above, the range "one or a plurality" is not limited as long as the effects of the present invention are achieved. The range may be, for example, 1 to 15, preferably 1 to 10, more preferably 1 to 5, still more preferably 1 to 4, particularly preferably 1 to 3, and still more particularly preferably 1 or 2.

A technique in which one or a plurality of the amino acids are deleted, substituted, and/or added in a specific amino acid sequence is known. For example, a peptide having an amino acid sequence in which one or a plurality of the amino acids are deleted, substituted, and/or added may be a peptide that achieves the effects of the present invention and that has an amino acid sequence with 50% or more identity to the amino acid sequence of: a peptide consisting of aspartic acid and/or glutamic acid residues; a peptide having more aspartic acid and/or glutamic acid residues than basic amino acid residues; a peptide having the amino acid sequence of any one of SEQ ID NOs: 1 to 4; or a peptide having two or more amino acid sequences of any of SEQ ID NOs: 1 to 4. In this peptide, the amino acid identity is generally 70% or more, preferably 80% or more, more preferably 90% or more, even more preferably 95% or more, particularly preferably 97% or more, and even more particularly preferably 98% or more.

The peptide is not limited as long as it has the characteristics described above. When a refolded antibody is immobilized on some kind of substrate, from the viewpoint of achieving easy immobilization of the antibody on the substrate, the above-described peptide that binds directly or through a linker to the inactive antibody and that has an isoelectric point lower than the isoelectric point of the inactive antibody (hereinafter sometimes referred to as a "low-isoelectric-point peptide") preferably further has an affinity for the substrate. For example, without limiting the present invention, a peptide consisting of the amino acid sequence of any one of SEQ ID NOs: 1 to 4 has an affinity for polycarbonate and/or polymethyl methacrylate. Thus, examples of the low-isoelectric-point peptide having an affinity for a substrate include a peptide having the amino acid sequence of any one of SEQ ID NOs: 1 to 4; a peptide having two or more amino acid sequences of any of SEQ ID NOs: 1 to 4; and a peptide having an amino acid sequence in which one or a plurality of the amino acids are deleted, substituted, and/or added in the amino acid sequence of these peptides, and having an affinity for polycarbonate and/or polymethyl methacrylate. The deletion, substitution, and/or addition of one or a plurality of amino acids are as described above, and the affinity, substrates, and binding conditions are as described later.

According to the present invention, the inactive antibody binding directly or through a linker to the peptide is not limited as long as the peptide binds to the inactive antibody directly or through a linker, and the binding region is also not limited. For example, it is possible for the inactive antibody to bind directly or through a linker to one or more of the peptides of one kind, or to the peptides of a plurality of kinds.

The binding region is not limited as long as the effects of the present invention are obtained. Examples thereof include a region that does not prevent exertion of the desired activity of the refolded antibody. To minimize adverse effects on the desired activity of the antibody, the peptide preferably binds to a region other than the variable region of the antibody, and more preferably a region outside the variable region of the antibody to the C-terminal and/or a region outside the variable region of the antibody to the N-terminal, and still more preferably a region outside the variable region of the antibody to the C-terminal.

The linker that can be used herein is not limited as long as the effects of the present invention are obtained, and a person skilled in the art may select a suitable linker within general consideration using a hitherto known technique. Examples of the linker include linkers called flexible linkers. The amino acid sequence of a widely used flexible linker is, for example, (G4S)n (e.g., n=1 to 4).

Regardless of whether the peptide described above has an affinity for a substrate, it is possible to use a peptide that has an affinity for a substrate (hereinafter sometimes referred to as an "affinity peptide") as a linker, so as to more easily immobilize the refolded antibody on a substrate as described above.

The affinity peptide is not limited as long as it does not limit the effects of the present invention, and as long as it has an affinity for a substrate. Examples include a peptide having the amino acid sequence of any one of SEQ ID NOs: 5 to 52, a peptide consisting of histidine, a TAT peptide, and the like.

For example, the peptides of SEQ ID NOs: 5 to 8 have an affinity for polycarbonate and/or polymethyl methacrylate; the peptides of SEQ ID NOs: 9 to 28 have an affinity for hydrophilic resins, such as hydrophilic polystyrene; the peptides of SEQ ID NOs: 29 to 52 have an affinity for silicon nitride; peptides consisting of histidine have an affinity for metals including divalent metals, such as nickel, zinc, copper, cobalt, and iron; and TAT peptides have an affinity for a phospholipid bilayer, such as cellular membrane. In view of this, these peptides have an affinity for polycarbonate and/or polymethyl methacrylate substrates, hydrophilic resin substrates, silicon nitride substrates, metal substrates, or substrates to which a phospholipid bilayer is attached. The details of the substrates are described below.

Other than the above, examples of the affinity peptide include a peptide having the amino acid sequence of any one of SEQ ID NOs: 5 to 52 in which one or a plurality of the amino acids are deleted, substituted, and/or added, and having an affinity for each of the above-described predefined substrates. The deletion, substitution, and/or addition of one or a plurality of the amino acids of the amino acid sequence are also as described above, and are not limited as long as the peptide has an affinity for a substrate. Of these, the peptides that fall under the category of the low-isoelectric-point peptides are preferably used as low-isoelectric-point peptides having an affinity for each of the above-described substrates.

It is possible for the affinity peptide to be linked to a region other than a region between the inactive antibody and the low-isoelectric-point peptide. It is possible for the affinity peptide to be further linked to any linker, such as a flexible linker mentioned above.

In the present invention, a cleavage site may be linked between the low-isoelectric-point peptide and the inactive antibody, and further between the low-isoelectric-point peptide, the affinity peptide, and the inactive antibody, so as to enable cleavage between the low-isoelectric-point peptide, the affinity peptide, and/or the antibody, if necessary. The cleavage method is not limited, and can be suitably selected by a person skilled in the art within general consideration using a hitherto known technique. Examples of cleavage include cleavage by a hitherto known restriction enzyme. In this case, for example, a site that can be cleaved by a restriction enzyme may be linked as necessary so that cleavage may be performed by a hitherto known restriction enzyme after refolding of the inactive antibody.

In the present invention, examples of the linkage between the low-isoelectric-point peptide and the inactive antibody, and further the affinity peptide, include, but are not limited to, inactive antibody-low-isoelectric-point peptide, inactive antibody-affinity peptide-low-isoelectric-point peptide, inactive antibody-low-isoelectric-point peptide-affinity peptide, inactive antibody-affinity peptide-low-isoelectric-point peptide-affinity peptide, affinity peptide-inactive antibody-low-isoelectric-point peptide, and the like.

Further, for example, when the low-isoelectric-point peptide has an affinity for a substrate, the refolded antibody is easily immobilized on the substrate via the low-isoelectric-point peptide. When the low-isoelectric-point peptide does not have an affinity for a substrate, the affinity peptide mentioned above may be linked so that the refolded antibody is easily immobilized on the substrate via the affinity peptide. Further, for example, in a structure such as inactive antibody-affinity peptide-low-isoelectric-point peptide, the low-isoelectric-point peptide may be cleaved off after refolding of the antibody so that the refolded antibody is easily immobilized on a substrate via the remaining affinity peptide.

In the present invention, whether a peptide has an affinity is determined based on whether the peptide can directly bind to a substrate. When a peptide directly binds to a substrate, this peptide has an affinity. Each peptide has a different affinity; therefore, to immobilize an antibody on a substrate via an affinity peptide, the antibody is more easily immobilized on a substrate by appropriately selecting the affinity peptide and the substrate.

Examples of the affinity peptide include those mentioned above. Examples of substrates suitable for these peptides include the above-mentioned polymethyl methacrylate substrates, polycarbonate substrates, hydrophilic resin substrates, silicon nitride substrates, and the like.

Regarding the substrates, more specifically, for example, "polymethyl methacrylate substrates" are not limited as long as a portion or the entire substrate surface has polymethyl methacrylate with no surface modification, and as long as a peptide having an affinity for the polymethyl methacrylate can bind to the polymethyl methacrylate surface. Examples of the polymethyl methacrylate substrates include substrates formed of polymethyl methacrylate; substrates in which polymethyl methacrylate is deposited on and/or covers a portion or the entire surface of a polymethyl methacrylate-free product; and the like. Further, for example, "hydrophilic resin substrates" are not limited as long as a portion or the entire substrate surface has a hydrophilic resin with no surface modification, and as long as a peptide having an affinity for the hydrophilic resin can bind to the hydrophilic resin surface. Examples of the hydrophilic resin substrates include substrates formed of hydrophilic resin; and substrates having a hydrophilic resin surface, such as a substrate in which a hydrophilic resin is deposited on and/or covers a portion or the entire surface of a hydrophilic resin-free product. Examples of hydrophilic resin include resins, such as hydrophilic polystyrene, hydrophilic polymethyl methacrylate, hydrophilic polycarbonate, hydrophilic polypropylene, hydrophilic polyethylene, and hydrophilic polydimethyl siloxane. When polystyrene, polypropylene, polyethylene, and the like, which are generally hydrophobic, are used in a substrate surface, the surface is subjected to hydrophilic treatment to be hydrophilic. The hydrophilic treatment may be performed in accordance with a hitherto known method, such as chemical treatment, electron irradiation treatment, ozone oxidation treatment, plasma treatment, corona treatment, and UV irradiation treatment. Further, for example, "silicon nitride substrates" are not limited as long as a portion or the entire substrate surface has silicon nitride with no surface modification, and as long as a peptide having an affinity for silicon nitride can bind to the silicon nitride surface. Examples of the silicon nitride substrates include substrates formed of silicon nitride; substrates in which silicon nitride is deposited on and/or covers a portion or the entire surface of a silicon nitride-free product; and the like. "Polycarbonate substrates," "metal substrates," and "substrates to which a phospholipid bilayer is attached" are also described as with the substrates described above, and a person skilled in the art can easily obtain these substrates.

The inactive antibody, the low-isoelectric-point peptide, the affinity peptide, and the like, may be produced by a hitherto known genetic engineering technique, a chemical synthesis, or the like. For example, the inactive antibody and the peptides may also be obtained from microorganisms having an ability to produce the antibody and/or the peptides through isolation and purification. The peptides may also be synthesized by a hitherto known chemical synthesis based on the information of the amino acid sequences of the peptides or based on the nucleotide sequences encoding the amino acid sequences. The chemical synthesis method encompasses a peptide synthesis method, such as liquid-phase peptide synthesis and solid-phase peptide synthesis. The affinity of the obtained peptide for a substrate may be determined based on whether the obtained peptide can directly bind to a substrate. If the obtained peptide directly binds to a substrate, this peptide has an affinity. The bonding conditions may be suitably determined in accordance with, for example, the type of the peptide to be used and the substrate to be used, or the antibody to be immobilized on the substrate. For example, the peptide may be brought into contact with a substrate in any buffer such as PBS; in this manner, it is determined whether the obtained peptide can directly bind to the substrate. An inactive antibody binding to a low-isoelectric-point peptide, or an inactive antibody further binding to an affinity peptide may be produced by using, for example, a crosslinking agent or an expression vector described later. A desired peptide may be obtained by inserting a polynucleotide encoding a low-isoelectric-point peptide and a polynucleotide encoding an antibody, and optionally a polynucleotide encoding an affinity peptide, into a vector or the like, followed by culture of a transformant containing the vector.

The isoelectric point of the entire "inactive antibody binding directly or through a linker to a peptide" used in the present invention differs depending an the isoelectric point of the antibody used, and is not limited as long as the effects of the present invention are obtained. For example, the isoelectric point of the entire "inactive antibody binding directly or through a linker to a peptide" is preferably 3.5 to 7.5, more preferably about 3.5 to 7, and still more preferably about 4 to 6.5.

Step (1-1) of the present invention is for denaturing an inactive antibody binding directly or through a linker to a peptide. The term "denature" as used herein refers to solubilization of the inactive antibody. For example, a drug capable of denaturing proteins, such as a denaturant, a chaotropic agent, i.e., a reducing agent, and a surfactant, may be caused to act on the inactive antibody so that the inactive antibody is denatured and solubilized. More specifically, examples of the drug include urea (e.g., 8 M), guanidine hydrochloride (e.g., 6 M), SDS (sodium lauryl sulfate, e.g., 1%), sodium thiocyanate (e.g., 4 M), potassium thiocyanate (e.g., 4 M), β-mercaptoethanol, dithiothreitol, and the like. More specifically, for example, the denaturation may be performed by causing the drug to act on the inactive antibody binding to a peptide. The denaturation of an inactive antibody in this manner is well known in the field of the present invention. The type and concentration of the drug capable of denaturing proteins, the time for denaturation, and the like, may be suitably determined by a person skilled in the art within general consideration using a hitherto known technique.

The inactive antibody used in the present invention refers to an antibody that does not sufficiently exert its specific activity. For example, when recombinant *Escherichia coli* or the like is used as a host to produce antibodies, most of the produced antibodies can be collected as inactive and insoluble aggregates (inclusion body). Examples of the inactive antibody of the present invention include such antibody aggregates (inclusion body).

In step (1-2) above, the peptide-binding inactive antibody denaturing in step (1-1) is dispersed in a liquid phase so that the inactive antibody is refolded to have desired activity. More specifically, in step (1-2) above, the peptide-binding inactive antibody in a state in which it is not immobilized on a solid phase such as a substrate is dispersed in a liquid phase; in this manner, the antibody is refolded to have desired activity. The solid phase is not particularly limited. Examples thereof include the above-mentioned polycarbonate and/or polymethyl methacrylate substrates, hydrophilic resin substrates, silicon nitride substrates, metal substrates, substrates to which a phospholipid bilayer is attached, gels, and the like. Examples of the dispersion of the denatured peptide-binding inactive antibody in a liquid phase include dispersion in a liquid phase by dilution, dispersion in a liquid phase by dialysis, dispersion in a liquid phase by gel chromatography, and the like. The dispersion is not limited as long as the modified inactive antibody binding directly or through a linker to the peptide is dispersed in a liquid phase.

The dispersion described above is not limited as long as the denatured peptide-binding inactive antibody is refolded. For example, in step (1-2), the modified peptide-binding inactive antibody may be dispersed in a liquid phase in a manner such that the concentration of the drug in contact with the peptide-binding inactive antibody immediately before being dispersed in a liquid phase is reduced to, for example, 1/10 to 1/100. The temperature and time for dispersion in a liquid phase may be suitably determined by a person skilled in the art. The dispersion may be performed in accordance with the Examples described later.

A solution that can be used in the dispersion in a liquid phase is not limited as long as the denatured peptide-binding inactive antibody is dispersed in a liquid phase, and as long as the inactive antibody is refolded. Examples of the solution include a buffer such as those used in the Examples described later. The ionic strength, the composition, etc., of the solution may be suitably determined as desired. Examples of the solution include solutions having a pH higher than, by 0.5 or more, preferably 0.5 to 4.5, more preferably 1 to 4, still more preferably by 1.5 to 4, the isoelectric point of the entire "inactive antibody binding directly or through a linker to the peptide". Although it is not limited as long as the effects of the present invention are obtained, as the ionic strength, the solution that can be used as a liquid phase in which the antibody is dispersed preferably has an NaCl concentration of, for example, 0 to 500 mM. Even when the ionic strength is low, it is possible to perform refolding with high efficiency; therefore, for example, the NaCl concentration is more preferably 0 to 300 mM, and still more preferably 0 to 150 mM.

In this regard, the present invention also provides a composition for refolding an antibody. The composition contains the inactive antibody binding directly or through a linker to the peptide, and more preferably contains the peptide-binding inactive antibody that is denatured as described above. The composition may further optionally contain a solution capable of refolding the peptide-binding inactive antibody, and preferably a solution having a pH higher than, by 0.5 or more, more preferably 0.5 to 4.5, still more preferably 1 to 4, and particularly preferably 1.5 to 4, the isoelectric point of the entire "inactive antibody binding directly or through a linker to the peptide". The use of this composition enables easier refolding of an inactive antibody. Considering that refolding proceeds within the composition, the composition can contain a refolded antibody.

In the present invention, the term "refolding" has the same meaning as that generally used in the field of the present invention. "Refolding" refers to a process in which an antibody in an inactive, aggregate state, i.e., an inclusion body, is made into a non-aggregate state (non-inclusion body) that can exert its specific activity. When an antibody in a non-aggregate state (non-inclusion body) is present in the liquid phase, it means that the inactive antibody has been refolded. Additionally, when an antibody having desired activity is present in the liquid phase, it means that the inactive antibody has been refolded.

In the present invention, refolding is performed efficiently. The refolding efficiency is determined by comparing the amount of antibody in an aggregate state (inclusion body) in the liquid phase with the amount of the antibody in a non-aggregate state (non-inclusion body). A larger amount of the antibody in a non-aggregate state (non-inclusion body) indicates a higher refolding efficiency. Referring to the Examples described later, the refolding efficiency may be determined by measuring the absorbance of the obtained liquid phase, or by comparing the antibody concentration in the liquid phase before centrifugation with the antibody concentration in the supernatant obtained after centrifugation. In the former case, a lower absorbance indicates a higher refolding efficiency. In the latter case, a higher antibody concentration in the supernatant obtained after centrifugation with respect to the antibody concentration in the liquid phase before centrifugation indicates a higher refolding efficiency. More specifically, for example, referring to the Examples using dialysis described later, the refolding efficiency may be determined by measuring the absorbance of a solution containing the antibody obtained after refolding, or by comparing the antibody concentration in a solution before centrifugation with the antibody concentration in the supernatant obtained after centrifugation, wherein the solution contains the antibody obtained after refolding. In the former case, a lower absorbance indicates a higher refolding efficiency. In the latter case, a higher antibody concentration in the supernatant obtained after centrifugation with respect to the antibody concentration in the liquid phase before centrifugation indicates a higher refolding efficiency. Furthermore, for example, referring to the Examples using gel chromatography described later, the refolding efficiency may be determined by comparing the antibody concentration (or weight) in a solution immediately before being loaded onto a column with the antibody concentration (or weight) obtained by elution from the column. A higher ratio of the latter to the former indicates a higher refolding efficiency.

As described above, in the present invention, the phrase "refolding an antibody in a liquid phase" indicates that the peptide-binding inactive antibody denatured in step (1-1) is subjected in step (1-2) to refolding in a state in which the antibody is not immobilized on a solid phase such as a substrate so that the antibody has desired activity. This method improves the efficiency of refolding of an inactive antibody, thus making it possible to produce antibodies having desired activity with high efficiency. In view of this, this method is also referred to be a method that improves the efficiency of refolding of an inactive antibody.

When the inactive antibody used herein is binding to a peptide having an affinity, the antibody after being subjected to refolding may be immobilized on a substrate via the peptide having an affinity in an easier, highly precise, and highly efficient manner, as described in the immobilizing method below. This contributes to the provision of a substrate on which a desired antibody is immobilized in a highly precise and highly efficient manner.

As described above, an inactive antibody is efficiently refolded when it binds to a low-isoelectric-point peptide. In this respect, the low-isoelectric-point peptide can be referred to as an auxiliary agent for refolding an antibody in a liquid phase. Therefore, the present invention also provides an auxiliary agent for refolding an antibody in a liquid phase, the agent consisting of a peptide having an isoelectric point lower than the isoelectric point of an antibody. This auxiliary agent is used to improve the efficiency for refolding the antibody. The auxiliary agent, i.e., the low-isoelectric-point peptide, is as described above.

As described above, an inactive antibody is efficiently refolded when it binds to a low-isoelectric-point peptide. Therefore, the present invention also provides an inactive antibody binding directly or through a linker to a low-isoelectric-point peptide, and provides a refolded antibody binding directly or through a linker to a low-isoelectric-point peptide. The low-isoelectric-point peptide, the antibody, and the like, are as described above.

2. Process for Producing Refolded Antibody

The process for producing a refolded antibody of the present invention comprises the steps of:
(2-1) denaturing an inactive antibody binding directly or through a linker to a peptide; and
(2-2) dispersing in a liquid phase the peptide-binding inactive antibody denatured in step (2-1) above.
In step (2-1), the peptide has an isoelectric point lower than the isoelectric point of the inactive antibody.

The peptide having an isoelectric point lower than the isoelectric point of the inactive antibody, the antibody, the inactive antibody, the inactive antibody binding directly or through a linker to a peptide, the linker, the denaturation, the liquid phase, the dispersion, the conditions of denaturation and dispersion, the refolding of an antibody, and the like, are as described above. When the affinity peptide is used as a linker, the substrates and the like are also as described above.

The production process above produces a refolded antibody. In particular, the production process above efficiently produces a refolded antibody.

In the antibody binding directly or through a linker to the peptide used in the production process, it is possible to cleave off an unnecessary peptide portion, if necessary. In this case, a cleavage site mentioned above may be linked to the antibody beforehand; after refolding, the unnecessary peptide portion may be cleaved off by a restriction enzyme or the like.

The production process of the present invention as described above efficiently produces the peptide-binding antibody, and the production process of the present invention is thus referred to be a process that improves the refolded-antibody-producing efficiency. When the thus-obtained refolded antibody is binding to a peptide having an affinity for a substrate, the antibody is easily immobilized on the substrate in a highly precise and highly efficient manner via the peptide having an affinity, as required. The present invention thus contributes to the provision of highly precise substrates for use in, for example, various types of analysis.

3. Method for Immobilizing a Refolded Antibody on a Substrate, and a Substrate on which a Refolded Antibody is Immobilized by this Method The method for immobilizing a refolded antibody on a substrate of the present invention comprises bringing an antibody refolded by the above-mentioned method for refolding an antibody in a liquid phase, and/or a refolded antibody obtained by the above-mentioned process for producing a refolded antibody into contact with a substrate.

The method for refolding an antibody in a liquid phase, the process for producing a refolded antibody, and the refolded antibody are as described above.

The method for immobilizing a refolded antibody on a substrate of the present invention comprises bringing the refolded antibody obtained as above into contact with a substrate to thereby immobilize the refolded antibody on the substrate. The immobilizing method of the present invention is not limited as long as the refolded antibody is immobilized on a substrate. From the viewpoint of achieving easier immobilization of an antibody, it is preferable that the refolded antibody being bound to the low-isoelectric-point peptide and/or affinity peptide be immobilized on a substrate via the low-isoelectric-point peptide and/or affinity peptide, and it is more preferable that the refolded antibody being bound to a peptide having an affinity for a substrate be immobilized on the substrate via the affinity peptide. From the viewpoint of far easier immobilization of the antibody, a peptide unnecessary for immobilization among the low-isoelectric-point peptide and/or affinity peptide that are linked to the antibody is preferably cleaved off by a restriction enzyme mentioned above before the antibody is brought into contact with a substrate. More specifically, for example, when the above-mentioned low-isoelectric-point peptide itself has an affinity for a substrate, the refolded antibody may be immobilized on a substrate via the low-isoelectric-point peptide. When the low-isoelectric-point peptide itself does not have an affinity for a substrate, a refolded antibody in which, for example, an antibody, an affinity peptide, and a low-isoelectric-point peptide are linked in this order may first be obtained, the low-isoelectric-point peptide is then separated from the antibody-affinity peptide by cleaving, and the resulting antibody-affinity peptide may be brought into contact with a substrate to thereby immobilize the refolded antibody on the substrate via the affinity peptide.

The expression "having an affinity" is as described above. Whether a peptide has an affinity is determined based on whether the peptide can directly bind to a substrate. When a peptide directly binds to a substrate, this peptide has an affinity. Each peptide has a different affinity; therefore, when an antibody is immobilized on a substrate via a peptide having an affinity, the peptide having an affinity and the substrate are suitably selected so that the antibody is more easily immobilized on the substrate. Examples of the peptide having an affinity include those mentioned above. Examples of substrates suitable for the peptide include substrates mentioned above, such as polymethyl methacrylate substrates, polycarbonate substrates, hydrophilic resin substrates, and silicon nitride substrates. These substrates are also as described above. The shape of the substrate is not limited as long as the peptide can bind to the substrate. For example, the substrate may be in any shape including a plate shape, a film (sheet) shape, a spherical shape, a granular (bead) shape, a fibrous shape, a microplate shape, or a cylindrical shape. When the substrate used in the present invention is used as a biochip, such as a protein chip, the silicon nitride substrate is preferably, for example, in the shape of a plate, film (sheet), or the like.

The contacting conditions are also as described above. For example, the contacting conditions used in the Examples described later may be used. A person skilled in the art may suitably determine the conditions based on the conditions used in the Examples. For example, a substrate may be brought into contact with any solution, such as a buffer (e.g., a PBS solution) containing an antibody binding to the peptide having an affinity for a certain period of time to allow the peptide to bind to the substrate. Alternatively, referring to the Examples described later, the solution may optionally be diluted, or the pH of the solution may optionally be adjusted, to allow the peptide to bind to the substrate.

The immobilizing method of the present invention makes it possible to easily and efficiently immobilize the recovered refolded antibody on a substrate. It is thereby possible to efficiently obtain a substrate on which the refolded antibody is immobilized. When the refolded antibody is binding to a peptide having an affinity for a substrate, it is possible to immobilize the antibody on the substrate via the peptide in an easier and highly dense manner, while maintaining the activity and further controlling its orientation to be more uniform. In view of this, it is possible for the present invention to immobilize a desired antibody in an easier, highly precise, and highly efficient manner. The immobilizing method of the present invention is capable of producing a substrate on which a desired refolded antibody is immobilized in an easier, highly precise, and highly efficient manner. The present invention thus makes it easy to produce biochips, such as protein chips, as well as packing materials for columns for, for example, an antigen-antibody reaction or enzyme reaction, microplates for use in ELISA, and the like. This indicates that the immobilizing method and the substrate of the present invention are useful in various fields, such as clinical examinations, drug discovery, environmental monitoring, and biochemistry.

4. Expression Vector, Transformant, and Antibody Binding to a Peptide Obtained from the Transformant The peptide-binding-antibody expression vector for refolding an antibody in a liquid phase of the present invention is characterized in that a polynucleotide encoding an antibody is linked directly or through a linker to a polynucleotide encoding a peptide having an isoelectric point lower than the isoelectric point of the antibody.

The peptide-binding-antibody expression vector is not particularly limited as long as it comprises the polynucleotide mentioned later and expresses the peptide-binding antibody in the host cell, based on the base sequence of the polynucleotide. The peptide-binding-antibody expression vector is used for the purpose of efficiently performing, in a liquid phase, refolding of an antibody that is expressed in this vector and that binds directly or through a linker to the peptide. The liquid phase, the antibody, the refolding, the antibody, the peptide having an isoelectric point lower than the isoelectric point of the antibody, the linker, and the like, are as described above. The polynucleotides are described below.

The polynucleotide encoding a peptide having an isoelectric point lower than the isoelectric point of an antibody used in the present invention is not limited as long as the isoelectric point of the expressed peptide is lower than the isoelectric point of the antibody binding directly or through a linker to this peptide. Examples thereof include polynucleotides encoding the low-isoelectric-point peptides described in section "1. Method for Refolding an Antibody in a Liquid Phase" above. The polynucleotides are not limited as long as they encode low-isoelectric-point peptides. Examples include a polynucleotide encoding a peptide consisting of aspartic acid and/or glutamic acid residues; a polynucleotide encoding a peptide having aspartic acid and/or glutamic acid residues more than basic amino acids residues; a polynucleotide encoding a peptide having the amino acid sequence of any one of SEQ ID NOs: 1 to 4, such as a polynucleotide having the base sequence of any one of SEQ ID NOs: 53 to 56, a polynucleotide having two or more base sequences of these polynucleotides; and the like. Examples further include a polynucleotide that hybridizes to a complementary strand of these polynucleotides under stringent conditions.

The expression "hybridizes to . . . under stringent conditions" means that two polynucleotide fragments hybridize to each other under standard hybridization conditions. The conditions are disclosed in Sambrook et al., Molecular Cloning: A Laboratory Manual (1989), Cold Spring Harbor Laboratory Press, New York, USA. More specifically, the "stringent conditions" refers to hybridization at about 45° C. in 6.0×SSC, followed by washing at 50° C. with 2.0×SSC. The polynucleotide that hybridizes to a complementary strand under stringent conditions generally has a certain degree or more of identity to the nucleotide sequences mentioned above. The polynucleotide has, for example, 70% or more, preferably 85% or more, more preferably 90% or more, further more preferably 95% or more, particularly preferably 98% or more, and yet more particularly preferably 99% or more, identity to the nucleotide sequences mentioned above. The identity of the nucleotide sequence may be confirmed using a commercially available analytical tool or an analytical tool available through telecommunication (e.g., the Internet). For example, software such as FASTA, BLAST, PSI-BLAST, or SSEARCH may be used for the calculation.

These polynucleotides may be produced by a hitherto known genetic engineering technique or chemical synthesis method (see, for example. Proc. Natl. Acad. Sci., USA., 78, 6613 (1981); Science, 222, 778 (1983); Molecular Cloning 2d Ed, Cold Spring Harbor Lab. Press (1989); and Lectures on Biochemical Experiments (Genetic Research Methods I, II, III), Journal of The Japanese Biochemistry Society (1986)). For example, a cDNA library is prepared from a suitable source, such as microorganisms comprising a desired polynucleotide, using a standard method, and the desired polynucleotide may be obtained from the library, by using a suitable probe or the like. A person skilled in the art may easily analyze or obtain a polynucleotide by a hitherto known technique, based on the amino acid sequence of the peptide. The amino acid sequences encoded by the polynucleotides of SEQ ID NOs: 53 to 56 correspond to the amino acid sequences of SEQ ID NOs: 1 to 4, respectively. For example, the polynucleotides may be easily produced or obtained by a hitherto known chemical DNA synthetic process, based on the information of the amino acid sequence of any one of SEQ ID NOs: 1 to 4, the information of the nucleotide sequence of any one of SEQ ID NOs: 53 to 56, the sequence information of the peptide described above, or the like.

A person skilled in the art may suitably select whether the polynucleotide encoding the antibody is linked to upstream or downstream of the polynucleotide encoding the low-isoelectric-point peptide, and whether the polynucleotide encoding the peptide is linked to the interior of the molecule of the antibody. In either case, the polynucleotide is preferably linked to a site that does not adversely affect the physiological activity and steric configuration of the antibody.

The peptide-binding-antibody expression vector of the present invention may further optionally be linked to the linker mentioned above and the cleavage site mentioned above. The base sequence encoding the linker is not limited as long as the effects of the present invention are achieved, and a person skilled in the art may suitably select within general consideration using a known technique. Examples of the linker include the flexible linkers mentioned above. A nucleotide sequence capable of suitably expressing the linker may be suitably connected to the linker.

When, in particular, an affinity peptide is used as a linker, the affinity peptide may be, for example, those mentioned above, and the polynucleotides encoding the affinity peptide are as described above. Examples of the polynucleotide encoding an affinity peptide include a polynucleotide encoding a peptide having the amino acid sequence of any one of SEQ ID NOs: 5 to 52, a polynucleotide having the base sequence of any one of SEQ ID NOs: 57 to 86, a polynucleotide encoding a peptide consisting of histidine, a polynucleotide encoding a TAT peptide, and the like. Examples further include a polynucleotide that hybridizes to a complementary strand of these polynucleotides under stringent conditions. The stringent conditions, the procedure for producing each polynucleotide, and the like, are as described above.

The binding region of, for example, a linker, such as an affinity peptide, to the peptide-binding-antibody expression vector is not limited as long as the effects of the present invention are achieved. It is preferably positioned under the control of the promoter. To allow the expression of, for example, an antibody, an affinity peptide, and a low-isoelectric-point peptide in this order, the polynucleotides may be linked in this order in the vector. At this time, the linker mentioned above and the cleavage site are optionally further suitably linked.

For example, the base sequence encoding a low-isoelectric-point peptide and the base sequence encoding a linker may be linked to any moiety, such as the 5' end and/or 3' end, of the polynucleotide encoding the antibody. To minimize adverse effects on the desired activity of the antibody, the polynucleotides encoding the peptide and linker are preferably linked to a region other than the base sequence encoding the variable region of the antibody, more preferably a region outside the base sequence encoding the variable region of the antibody to the 5' end and/or a region outside the base sequence encoding the variable region of the antibody to 3' end, and still more preferably a region outside the base sequence encoding the variable region of the antibody to the 3' end.

As is hitherto known, a vector is generally suitably selected in relation to the host cell. More specifically, the vector used in the present invention is not limited as long as it is an expression vector generally used in the genetic engineering field. Examples thereof include plasmid vectors, such as pBR, pUC, pCD, pET, pGEX, pCMV, pMSG, and pSVL derived from bacteria such as $E.$ $coli$ or from yeast; and viral vectors derived from retrovirus, adenovirus, vaccinia virus, baculovirus, bacteriophage, etc. As described above, these vectors may be suitably selected in relation to the host cell.

A promoter is optionally linked to these vectors. The promoter is not limited as long as it is suitable for the host cell, and a hitherto known promoter may be used. Examples of the promoter include lac promoter, trp promoter, tac promoter, trc promoter, racA promoter, λPL promoter, lpp promoter, T7 promoter, and the like, and these promoters are used, for example, when $E.$ $coli$ is used as the host cell. Other examples of the promoter include SV40 promoter, (CV promoter, RSV promoter, HSV-TK promoter, LTR promoter, SRα promoter, EF-1α promoter, and the like. These promoters are used when animal cells are used as the host cells. In consideration of the relationship with the host cell, the following promoters may also be used: yeast cell promoters, insect cell promoters, viral promoters, and the like. When a vector has an endogenous promoter therein, the endogenous promoter may also be used.

The promoter-binding site in the peptide-binding-antibody expression vector of the present invention is not limited, as long as the peptide-binding antibody is expressed in the host cell. Generally, the promoter is connected to a site upstream in the base sequence of a polynucleotide encoding the peptide-binding antibody. More specifically, in the peptide-binding-antibody expression vector of the present invention, the polynucleotide encoding the peptide-binding antibody is under the control of the promoter.

As the host cell, hitherto known prokaryotic cells and eukaryotic cells may be used. Examples thereof include $E.$ $coli,$ $Bacillus$ $subtilis,$ $Streptococcus,$ $Staphylococcus,$ actinomycetes, filamentous fungi, and like bacteria; yeast and $Aspergillus;$ $Drosophila$ S2, $Spodoptera$ Sf9, and like insect cells; and L cells, CHO cells, COS cells, Art-20 cells, HeLa cells, C127 cells, myeloma cells, GH3 cells, FL cells, VERO cells, CV-1 cells, Bowes melanoma cells, oocytes of platanna, and like animal or plant cells.

These vectors, promoters, and host cells may be suitably combined based on the common general technical knowledge in this field. Examples of combinations include pET (T7 promoter)/$E.$ $coli$ BL21 (DE3), and pGEX (Tac promoter)/$E.$ $coli$ BL21.

In the peptide expression vector of the present invention, base sequences of an enhancer, splicing signal, poly-A additional signal, drug resistance gene, Green Fluorescent Protein (GFP), or other marker genes may further be connected. These base sequences may be connected at any site of the expression vector, depending on the purpose.

The peptide-binding-antibody expression vector of the present invention may be prepared using a method hitherto known in this field, by positioning necessary base sequences, such as a polynucleotide encoding the peptide and a polynucleotide encoding the antibody, on a suitable site of the vector using a restriction enzyme or the like. The use of these expression vectors makes it possible to easily obtain an antibody to which a desired peptide binds.

The present invention provides a transformant obtained by transforming a host cell by introducing the peptide-binding-antibody expression vector thereinto. In the present invention, examples of the host cell include those described above. The method for obtaining a transformant by introducing the peptide-binding-antibody expression vector into the host cell is not particularly limited, and a hitherto known general method may be used. For example, the transformant may be formed by various methods described in standard laboratory manuals. Specific examples thereof include a calcium chloride method; a rubidium chloride method; transfection using a DEAE-dextran; microinjection; cationic lipid-mediated transfection using, for example, a liposome; electroporation; transduction; and infection by bacteriophage.

The present invention also provides a peptide-binding antibody that can be obtained from the transformant. The transformant, the peptide, and the antibody are as described above. In the present invention, the peptide-binding antibody is a peptide-fused antibody in which the peptide and the antibody are linked to be unified as described above.

In the present invention, the peptide-binding antibody may be prepared by culturing the transformant in a suitable culture medium, and recovering the desired peptide-fused antibody from the transformant and/or culture. The culture and recovery methods are not particularly limited, and hitherto known general methods may be used. For example, culture may be performed by passage culture or batch culture using any culture medium suitable for the host cell. The culture may be continued until an adequate amount of peptide-fused antibody is obtained using the amount of the protein produced inside and outside of the transformant as an index. The culture medium used in the culture may be suitably selected from various commonly used culture media depending on the host cell. The culture conditions, such as temperature and time, may also be suitably selected from known conditions depending on the host cell.

The peptide-fused antibody thus obtained may be further isolated or purified, if necessary, by various isolation operations based on its physical properties, chemical properties, and the like. Examples of the isolation operations include solvent extraction, distillation, and various types of chromatography (see Biochemistry Data Book II, pp. 1175-1259, First Edition, First Printing, 1980, Kagaku-Dojin Publishing Co., Inc., Tokyo; Biochemistry, 25 (25), 8274 (1986); and Eur. J. Biochem., 163, 313 (1987)).

The thus-obtained peptide-fused antibody is preferably used in the method for refolding an antibody in a liquid phase, and in the process for producing a refolded antibody.

EXAMPLES

The following describes the present invention with reference to Examples; however, the present invention is not limited to the following Examples.

Test Example 1

Evaluation of Anti-CEA scFv Refolding Efficiency

1. In accordance with the following procedures, inactive antibodies binding to a peptide having an isoelectric point lower than the isoelectric point of the inactive antibodies were prepared. These inactive antibodies have the following structures, i.e., Examples 1-1 to 1-3 and Comparative Example 1.

In Example 1-1, a peptide (PM) having the amino acid sequence of SEQ ID NO: 4 and a histidine residue (His) were linked in a linear manner to a single-chain antibody (anti-CEA scFv) against a carcinoembryonic antigen (CEA). Examples 1-2 and 1-3 had the same structure as that of Example 1-1, except that a peptide consisting of 5 aspartyl residues (D5) and a peptide consisting of 10 aspartyl residues (D10) were used, respectively, in place of the peptide having the amino acid sequence of SEQ ID NO: 4 used in Example 1-1. Comparative Example 1 had the same structure as that of Example 1, except that the peptide having the amino acid sequence of SEQ ID NO: 4 was not linked. The "isoelectric point" used in the test example is a value calculated based on the amino acid sequences of the peptide-binding antibodies of Examples 1-1 to 1-3 and the amino acid sequence of the histidine-binding antibody of Comparative Example 1, and is a value calculated by inputting the amino acid sequence in the commercially available software Genetyx ver. 6 (produced by Genetyx Corporation) in accordance with the procedure of the software.

Example 1-1: anti-CEA scFv-PM-His (isoelectric point: 4.9)
Example 1-2: anti-CEA scFv-D5-His (isoelectric point: 4.7)
Example 1-3: anti-CEA scFv-D10-His (isoelectric point: 4.4)
Comparative Example 1: anti-CEA scFv-His (isoelectric point: 5.3)

First, a nucleotide sequence in which the polynucleotide encoding 6 histidine residues were linked to the 3' end of the polynucleotide (SEQ ID NO: 56) encoding the peptide having the amino acid sequence of SEQ ID NO: 4 was synthesized and introduced into the NotI/XhoI site of pET22 vector (produced by Merck & Co., Inc.). Thereafter, anti-CEA scFv was amplified by PCR, and introduced into the NdeI/NotI site of the vector. In this manner, an expression vector for producing Example 1-1 was obtained. In this expression vector, a T7 promoter/Lac operator, RBS, a start codon (ATG)-anti-CEA scFv, the peptide, a stop codon, and a T7 terminator were linked in this order. Then, expression vectors for producing Examples 1-2 and 1-3 were obtained in a manner similar to the above, except that a polynucleotide encoding a peptide consisting of 5 contiguous aspartyl residues or a polynucleotide encoding a peptide consisting of 10 contiguous aspartyl residue was used in place of the polynucleotide encoding the peptide having the amino acid sequence of SEQ ID NO: 4. Further, an expression vector for producing Comparative Example 1 was obtained as in Example 1-1, except that a polynucleotide encoding the peptide having the amino acid sequence of SEQ ID NO: 4 was not used.

Rosetta® DE3 Competent Cells (produced by Novagen) were transformed by using each of the thus-obtained expression vectors, and cultured in LB-agar plates containing ampicillin and chloramphenicol to form colonies. The colonies were collected and inoculated into 10 mL of 2×YT medium (containing ampicillin and chloramphenicol), and subjected to shaking culture overnight at 200 rpm at 37° C., thereby obtaining a cultured medium. Subsequently, 50 mL of Overnight Express™ TB Instant Medium (produced by Merck & Co., Inc.) was placed into a 500-mL flask with a baffle. Further, ampicillin, chloramphenicol, and the cultured medium were added thereto so that OD=0.1, followed by shaking culture at 37° C. at 200 rpm for 24 hours.

After culture, the cells were collected by centrifugation, and 5 mL of PBS (137 mM of NaCl, 2.7 mM of KCl, 8.1 mM of $Na_2HPO_4$, and 1.47 mM of $KH_2PO_4$ (pH of 7.4)) was added thereto, followed by ultrasonic disruption. The inclusion body was then collected by centrifugation, washed with distilled water 3 times, and freeze-dried. In this manner, the peptide-binding inactive antibody in a powder form was obtained.

The thus-obtained inclusion body powder was solubilized in a 6 M guanidine hydrochloride solution (25° C., 10 minutes), and the supernatant was collected by centrifugation (25° C., 10,000 rpm, 15 minutes). Subsequently, an His-Trap HP column (produced by GE healthcare) was equilibrated with 2×PBS containing 8 M urea and 20 mM imidazole, and the supernatant obtained as described above was supplied thereto so that the peptide-binding antibody was adsorbed onto the column, followed by elution with 2×PBS containing 8 M urea and 0.4 M imidazole. The obtained eluate was dialyzed with PBS containing 8 M urea, thereby obtaining a solution containing the peptide-binding inactive antibody at a final concentration of 500 µg/mL.

The liquid phase for refolding described later was prepared within a BD Flacon® 96-well microplate well (produced by Nippon Becton Dickinson Company, Ltd.), and the peptide-binding inactive antibody modified as described above was dispersed in each well so that the final concentration was 200 µg/mL (0.5 M Uera) (entire volume: 200 uL).

Regarding the liquid phase for refolding, referring to the accompanying figures, a liquid phase having a pH of 6 was prepared by using 0.05 M MES Good's buffer (trade name, MES (2-(N-morpholino) ethanesulfonic acid) produced by Nacalai Tesque, Inc.) and by optionally adding NDSB and/or NaCl; a liquid phase having a pH of 6.5 was prepared by using 0.05 M ADA Good's buffer (trade name, ADA (N-(2-acetamido)iminodiacetic acid)) produced by Nacalai Tesque, Inc.) and by optionally adding NDSB and/or NaCl; a liquid phase having a pH of 7 was prepared by using 0.05 M MOPS Good's buffer (trade name, MOPS (3-(N-morpholino)propanesulfonic Acid) produced by Nacalai Tesque, Inc.) and by optionally adding NDSB and/or NaCl; a liquid phase having a pH of 7.5 was prepared by using 0.05 M HEPES Good's buffer (trade name, HEPES (2-[4-(2-hydroxyethyl)-1-piperazinyl]ethanesulfonic acid) produced by Nacalai Tesque, Inc.) and by optionally adding NDSB and/or NaCl; a liquid phase having a pH of 8 was prepared by using 0.05 M EPPS Good's buffer (trade name, EPPS (N-(2-hydroxyethyl)piperazine-N'-3-propanesulfonic acid) produced by Nacalai Tesque, Inc.) and by optionally adding NDSB and/or NaCl; and a liquid phase having a pH of 8.5 was prepared by using 0.05 M TAPS Good's buffer (trade name, TAPS (N-tris(hydroxymethyl)methyl-3-aminopropanesulfonic acid) produced by Nacalai Tesque, Inc.) and by optionally adding NDSB and/or NaCl. In the figures, the pH (6.0 to 7.5), the NDSB (1-(3-sulfonatopropyl)pyridinium, 0 M or 0.5 M), and the NaCl concentration (0 to 300 mM) of each liquid phase are values obtained after the peptide-binding inactive antibody was dispersed in the microplate wells.

After the dispersion as described above, the absorbance at a wavelength of 450 nm was measured, while incubating at an ordinary temperature, by using a microplate reader every 30 minutes for 6 hours in total after the incubation was started. The obtained absorbance was used as an index of aggregate for evaluation. A higher absorbance indicates more aggregates, i.e., more antibodies remaining without being refolded.

Figure 2:
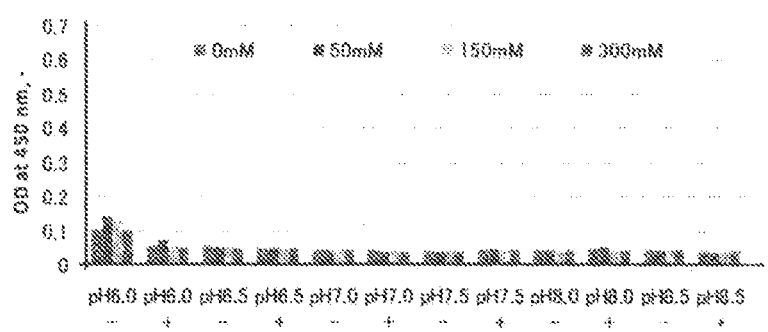
FIG. 2 is graphs showing the results of refolding of an anti-CEA antibody.
Figure 2:
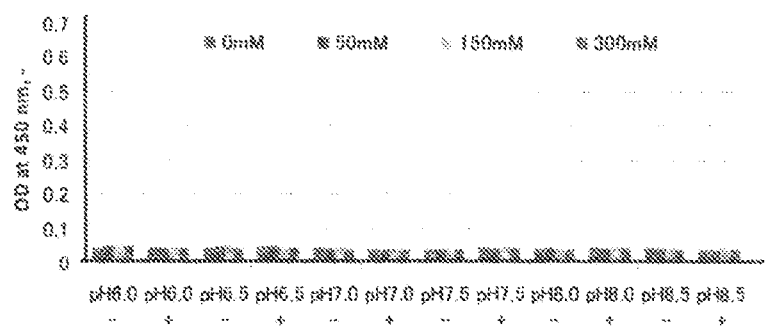

2. FIGS. 1 and 2 show the results. Both of the figures show the measurement results obtained after incubation for 6 hours.

FIG. 1 shows the results obtained when Example 1-1 (anti-CEA scFv-PM-His) and Comparative Example 1 (anti-CEA scFv-His) were used. As is clear from FIG. 1, the OD values of Example 1-1 were remarkably smaller than those of Comparative Example 1. In FIG. 1, a smaller OD value indicates a reduced amount of inactive and insoluble antibody aggregate. That is, a smaller OD value indicates a higher refolding efficiency. In FIG. 1, for example, pH 6.0– and 0 mM indicate that refolding was performed by dispersing the antibody in a liquid phase that has a pH of 6 and that is NDSB-free with 0 mM NaCl; and pH 6.0+ and 50 mM indicates that refolding was performed by dispersing the antibody in a liquid phase that has a pH of 6 and that contains 0.5 M NDSB and 50 mM NaCl. In the figure, for example, four bars each are shown at "pH 6.0–" and "pH 6.0+." These bare represent 0 mM, 50 mM, 150 mM, and 300 mM NaCl in order from left, i.e., in order from the smallest number from 1 to 4 shown above the bars at "pH 6.0–" in the graph showing the results of Comparative Example 1 (anti-CEA scFv-His) in FIG. 1. The same applies to the following figures similar to FIG. 1.

Although not shown in the figures, even when the antibody was dispersed in the liquid phase having a pH of 8 or 8.5, the result was as excellent as that obtained with a pH of 7 in Example 1-1, regardless of the addition of NDSB and the NaCl concentration.

FIG. 2 shows the effects obtained when Examples 1-2 and 1-3 were used. As is clear from FIG. 2, the OD values obtained with respect to both Examples 1-2 and 1-3 were remarkably smaller than those of Comparative Example 1.

The above confirms that when an inactive antibody binding to a peptide having an isoelectric point lower than the isoelectric point of the inactive antibody is denatured and dispersed in a liquid phase, the antibody refolding efficiency remarkably improves, compared with the case where an antibody not binding to the peptide was used.

Test Example 2

Evaluation of Anti-RNase scFv Refolding Efficiency

1. In accordance with the following procedures, inactive antibodies binding to a peptide having an isoelectric point lower than the isoelectric point of the inactive antibodies were prepared. These inactive antibodies have the following structures, i.e., Examples 2-1 to 2-5 and Comparative Example 2.

Example 2-1: anti-RNase scFv-PM-His (isoelectric point: 5.96)
Example 2-2: anti-RNase scFv-D5-His (isoelectric point: 5.75)
Example 2-3: anti-RNase scFv-D10-His (isoelectric point: 4.93)
Example 2-4: anti-RNase scFv-D15-His (isoelectric point: 4.55)
Example 2-5: anti-RNase scFv-D20-His (isoelectric point: 4.32)
Comparative Example 2: anti-RNase scFv-His (isoelectric point: 7.26)

Inactive antibodies binding to a peptide having an isoelectric point lower than the isoelectric point of the inactive antibodies were prepared (Examples 2-1 to 2-3 and Comparative Example 2), as in Examples 1-1 to 1-3 and Comparative Example 1 of Test Example 1, except that a single-chain antibody against RNase was used as an antibody.

Further, inactive antibodies binding to a peptide having an isoelectric point lower than the isoelectric point of the inactive antibodies were prepared (Examples 2-4 and 2-5) as in Example 1-2 of Test Example 1, except that a single-chain antibody against RNase was used as an antibody, and a peptide consisting of 15 aspartyl residues (D15) or a peptide consisting of 20 aspartyl residues (D20) was used in place of the peptide consisting of 5 aspartyl residues. In this preparation, the expression vectors for preparing Examples 2-4 and 2-5 were used, wherein the expression vectors were obtained as above, except that a polynucleotide encoding a peptide consisting of 15 contiguous aspartyl residues or a polynucleotide encoding a peptide consisting of 20 contiguous aspartyl residues was used in place of the polynucleotide encoding a peptide consisting of 5 contiguous aspartyl residues used in Example 1-2.

Subsequently, denaturation and refolding were performed with respect to the antibodies of Examples 2-1 to 2-5 and Comparative Example 2, following the same procedures of Test Example 1, and the absorbance was evaluated using a microplate reader.

Figure 3:
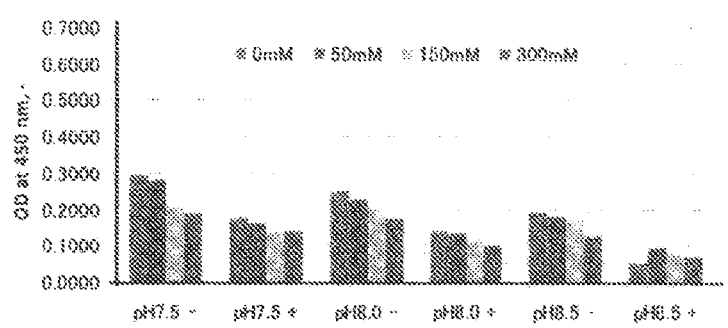
FIG. 3 is graphs showing the results of refolding of an anti-RNase antibody.
Figure 3:
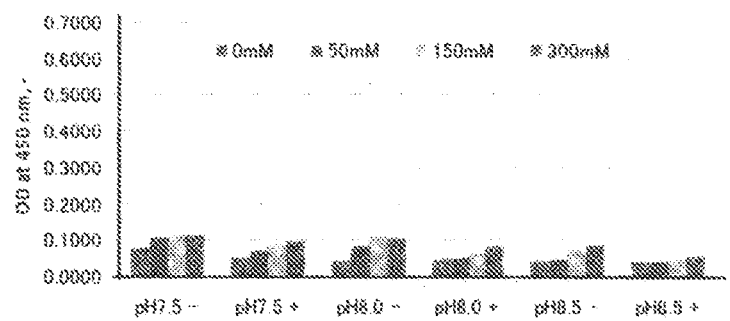
Figure 4:
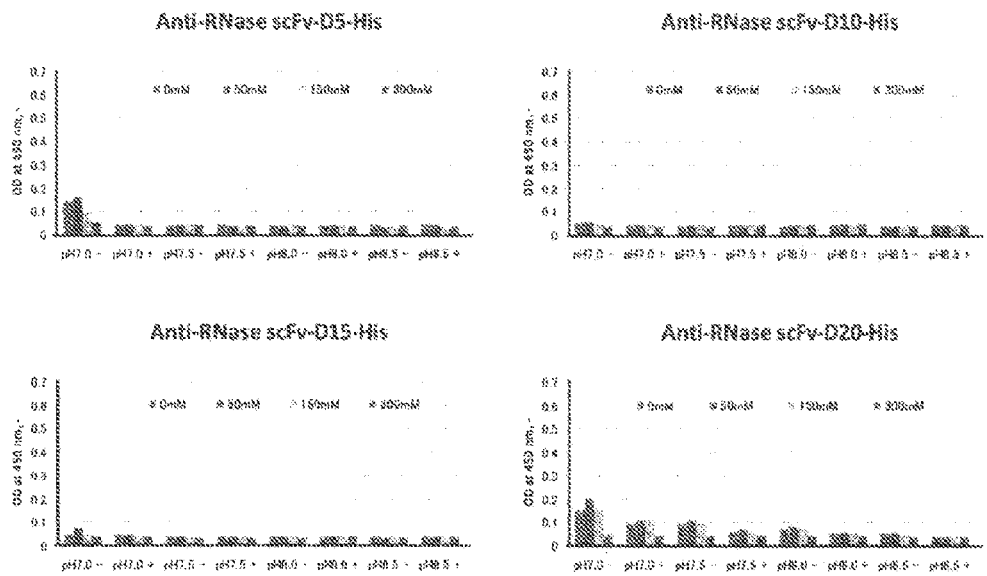
FIG. 4 is graphs showing the results of refolding of an anti-RNase antibody.

2. FIGS. 3 and 4 show the results.

FIG. 3 shows the effects obtained when Example 2-1 and Comparative Example 2 were used. As is clear from FIG. 3, the CD values of Example 2-1 were remarkably smaller than those of Comparative Example 2.

FIG. 4 shows the effects obtained when Examples 2-2 to 2-5 were used. As is clear from FIG. 4, the OD values of any of Examples 2-2 to 2-5 were remarkably smaller than those of Comparative Example 2.

The above confirms that when an inactive antibody binding to a peptide having an isoelectric point lower than the isoelectric point of the inactive antibody is denatured and dispersed in a liquid phase, the antibody refolding efficiency remarkably improves, compared with the case where an antibody not binding to the peptide was used.

Test Example 3

Evaluation of Anti-CRP scFv Refolding Efficiency

1. In accordance with the following procedures, inactive antibodies binding to a peptide having an isoelectric point lower than the isoelectric point of the inactive antibodies were prepared. These inactive antibodies have the following structures, i.e., Examples 3-1 to 3-5 and Comparative Example 3. The test was performed as in Test Example 2, except that a single-chain antibody against a C-reactive protein (CRP), which is different from the antibody used in Test Example 2, was used.

Example 3-1: anti-CRP scFv-PM-His (isoelectric point: 5.9)
Example 3-2: anti-CRP scFv-D5-His (isoelectric point: 5.8)
Example 3-3: anti-CRP scFv-D10-His (isoelectric point: 5)
Example 3-4: anti-CRP scFv-D15-His (isoelectric point: 4.6)
Example 3-5: anti-CRP scFv-D20-His (isoelectric point: 4.4)
Comparative Example 3: anti-CRP scFv-His (isoelectric point: 6.6)

Figure 5:
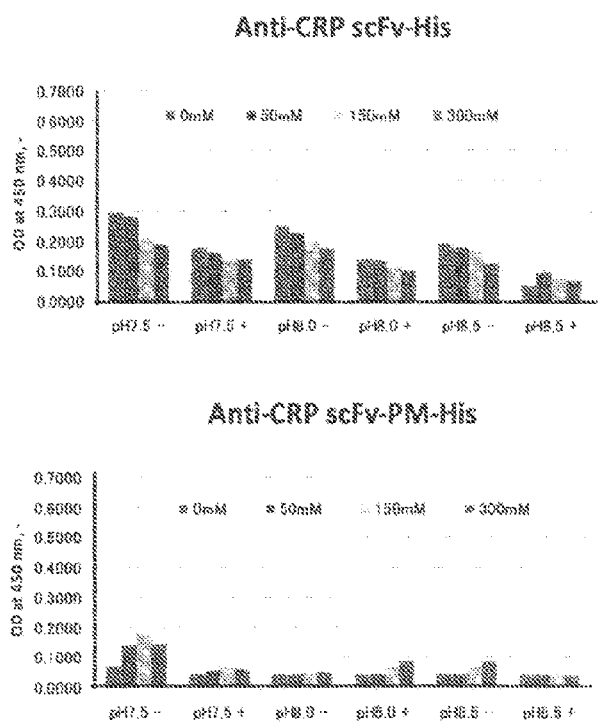
FIG. 5 is graphs showing the results of refolding of an anti-CRP antibody.
Figure 6:
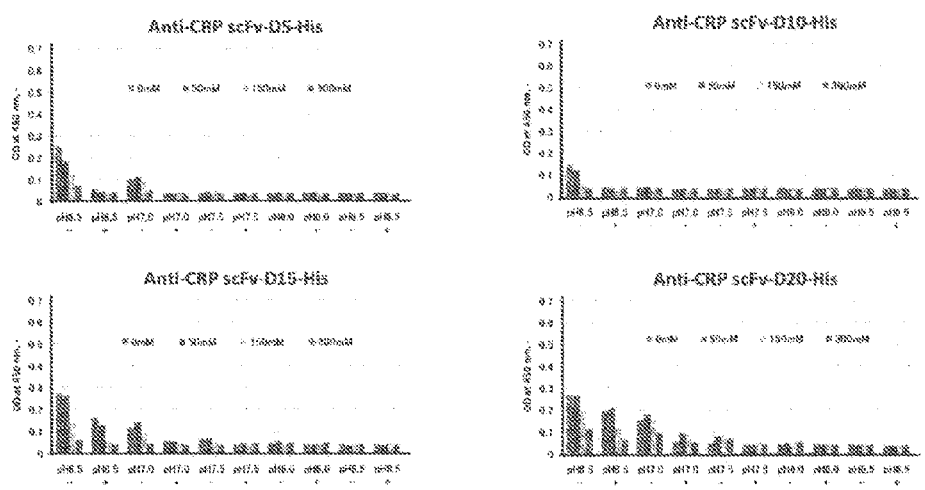
FIG. 6 is graphs showing the results of refolding of an anti-CRP antibody.

2. FIGS. 5 and 6 show the results.

FIG. 5 shows the effects obtained when Example 3-1 and Comparative Example 3 were used. As is clear from FIG. 5, the OD values of Example 3-1 were remarkably smaller than those of Comparative Example 3.

FIG. 6 shows the effects obtained when Examples 3-2 to 3-5 were used. As is clear from FIG. 6, the OD values of any of Examples 3-2 to 3-5 were remarkably smaller than those of Comparative Example 3.

The above confirms that when an inactive antibody binding to a peptide having an isoelectric point lower than the isoelectric point of the inactive antibody is denatured and dispersed in a liquid phase, the antibody refolding efficiency remarkably improves, compared with the case where an antibody not binding to the peptide was used.

Test Example 4

Evaluation of Refolding Efficiency of scFv with Anti-TSH, Anti-IgA, Anti-IgG, or Anti-TF189

1. Inactive antibodies binding to a peptide having an isoelectric point lower than the isoelectric point of the inactive antibodies were prepared as in Example 1, except that TSH, IgA, IgG, or TF189 was used as an antibody. These inactive antibodies have the following structures, i.e., Examples 4 to 7:

Example 4: anti-TSH scFv-PM-His (isoelectric point: 6.41)
Example 5: anti-IgA scFv-PM-His (isoelectric point: 6.49)
Example 6: anti-IgG scFv-PM-His (isoelectric point: 6.14)
Example 7: anti-TF189 scFv-PM-His (isoelectric point: 5.86)

Figure 7:
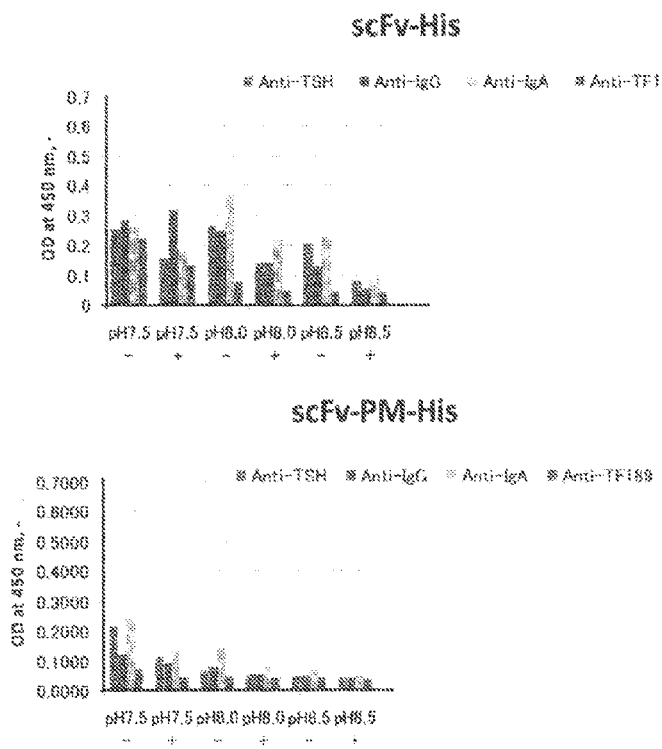
FIG. 7 is graphs showing the results of refolding of each antibody (anti-TSH antibody, anti-IgA antibody, anti-IgG antibody, and anti-TF189 antibody).

2. FIG. 7 shows the results.

As shown in FIG. 7, even when a single-chain antibody TSH, IgA, IgG, or TF189 was used as an antibody, the refolding efficiency was increased by allowing the peptide to bind to the antibody. In the graphs, four bars are shown at, for example, "pH7.5−" and "pH7.5+." These bars represent the results of TSH, IgA, IgG, and TF189, in order from left. The graphs show the results obtained when refolding was performed by dispersing the antibody in a solution having an ionic strength (NaCl concentration) of 0 mM.

Test Example 5

Calculation of Refolding Efficiency

The inactive antibodies of Example 1-1, Example 2-1, Example 3-1, Example 4, and Comparative Example 1 were denatured and refolded as follows to calculate the refolding efficiency of these antibodies.

More specifically, each of the peptide-binding inactive antibodies was diluted in PBS containing 8 M urea so that the final concentration was 500 µg/mL. Each of the peptide-binding inactive antibodies denatured in this manner was dispersed in a liquid phase (0.05 M TAPS Good's buffer, pH 8.5, NDSB201-free, NaCl concentration: 0 mM) by dialysis for 18 hours (final concentration: 0.5 M Uera). Then, centrifugation was performed at 10000 g at 25° C. for 2 minutes, and the supernatant was collected. The antibody concentrations before and after the centrifugation were quantified using a DC™ Protein Assay Kit (produced by Bio-Rad Laboratories), and the antibody concentration in the supernatant collected after the centrifugation was divided by the antibody concentration in the liquid phase before the centrifugation to calculate the recovery.

The results confirmed that the refolding efficiency of Example 1-1 was 91.2%, which is more than twice the refolding efficiency of Comparative Example 1, which was 43.9%. The refolding efficiency of Example 2-1 was 88%, Example 3-1 was 90%, and Example 4 was 93%, which are all considered high efficiency.

Test Example 6

Immobilization of Refolded Antibody on a Substrate

1. The peptide (PM) having the amino acid sequence of SEQ ID NO: 4 has an affinity for a polymethyl methacrylate (PMA) substrate. In Example 2-1, this peptide bound to the single-chain antibody; therefore, the refolded antibody binding to the peptide having the amino acid sequence of SEQ ID NO: 4 obtained as above was brought into contact with a polymethyl methacrylate substrate to analyze whether the refolded antibody was satisfactorily immobilized on the substrate via this peptide. As a comparative example, Comparative Example 2 that was refolded was used. In the refolding, a liquid phase prepared by using 0.05 M TAPS Good's buffer and to have a pH of 8.5 with no addition of NDSB201 and a NaCl concentration of 0 mM was used.

More specifically, each antibody obtained after refolding was serially diluted two-fold in PBS, and 100 µL each of the resulting product was added to a polymethyl methacrylate microplate and incubated at 4° C. overnight. Thereafter, the microplate was washed with PBST (PBS-0.1% Tween 20), and 300 µL each of 2% BSA-PBST was added and incubated at 25° C. for 1 hour. After the plate was washed with PBST, 100 µL each of biotinylated RNase (antigen) diluted in 2% BSA-PBST to 100 ng/mL was added and incubated at 25° C. for 1 hour. After the plate was washed with PEST, 100 µL each of HRP-labeled streptavidin diluted 5000-fold in 2% BSA-PBST was added and incubated at 25° C. for 1 hour. After washing with PBST, 100 µL each of TMB substrate solution was added and incubated at 25° C. for 15 minutes; thereafter, 100 µL each of 0.3 M $H_2SO_4$ was added to stop the coloring reaction. The absorbance at a wavelength of 450 nm (sub-wavelength of 650 nm) was measured using a microplate reader.

Figure 8:
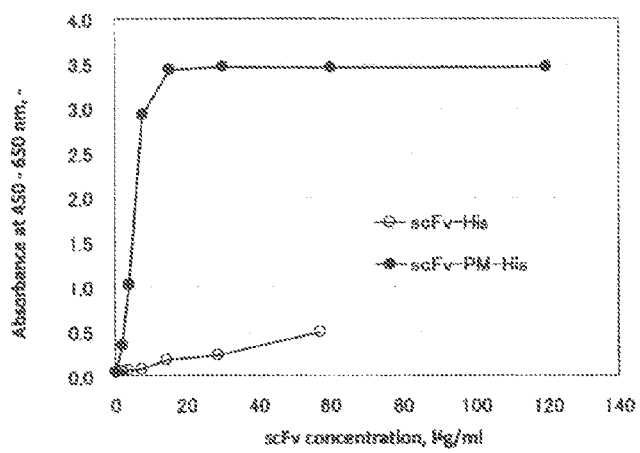
FIG. 8 is a graph showing the results obtained by immobilizing a refolded antibody on a substrate (PM).

2. FIG. 8 shows the results.

As is clear from the results, when Example 2-1 was used, the activity on the substrate improved in a manner dependent on the concentration of the refolded antibody. In contrast, when Comparative Example 2, to which the peptide was not bound, was used, the activity based on the refolded antibody was remarkably low. These results confirm that the peptide used in Example 2-1 maintained its excellent and specific affinity for polymethyl methacrylate even after the antibody was subjected to denaturation and refolding, and that the antibody refolded as described above also sufficiently maintained its characteristic activity.

Test Example 7

Evaluation of Efficiency of Refolding of an Antibody to which a Low-Isoelectric-Point Peptide and an Affinity Peptide are Bound 1. The antibody refolding efficiencies were compared as in Test Example 2, except that the following affinity peptides were linked in addition to the peptide used in Example 2-4. The PS below is an affinity peptide consisting of the amino acid sequence of SEQ ID NO: 10 and having an affinity for hydrophilic polystyrene. The SiN below is an affinity peptide consisting of the amino acid sequence of SEQ ID NO: 29 and having an affinity for silicon nitride. In Example 8-1, a cleavage site that can be cut by an enzyme was linked between PS and D15. In Example 8-2 as well, a cleavage site was linked between SiN and D15. The antibodies to which each of the affinity peptides above was linked in place of the low-isoelectric-point peptide of Example 2-4 were considered as Comparative Example 4 (PS) and Comparative Example 5 (SiN). A polynucleotide encoding the amino acid sequence of SEQ ID NO: 10 is represented by SEQ ID NO: 61, and a polynucleotide encoding the amino acid sequence peptide of SEQ ID NO: 29 is represented by SEQ ID NO: 63.

Example 2-4: anti-RNase scFv-D15-His (isoelectric point: 4.55)

Example 8-1: anti-RNase scFv-PS-D15-His (isoelectric point: 5)

Example 8-2: anti-RNase scFv-SiN-D15-His (isoelectric point: 4.83)

Comparative Example 2: anti-RNase scFv-His (isoelectric point: 7.26)

Comparative Example 4: anti-RNase scFv-PS-His (isoelectric point: 8.97)

Comparative Example 5: anti-RNase scFv-SiN-His (isoelectric point: 8.14)

Figure 9:
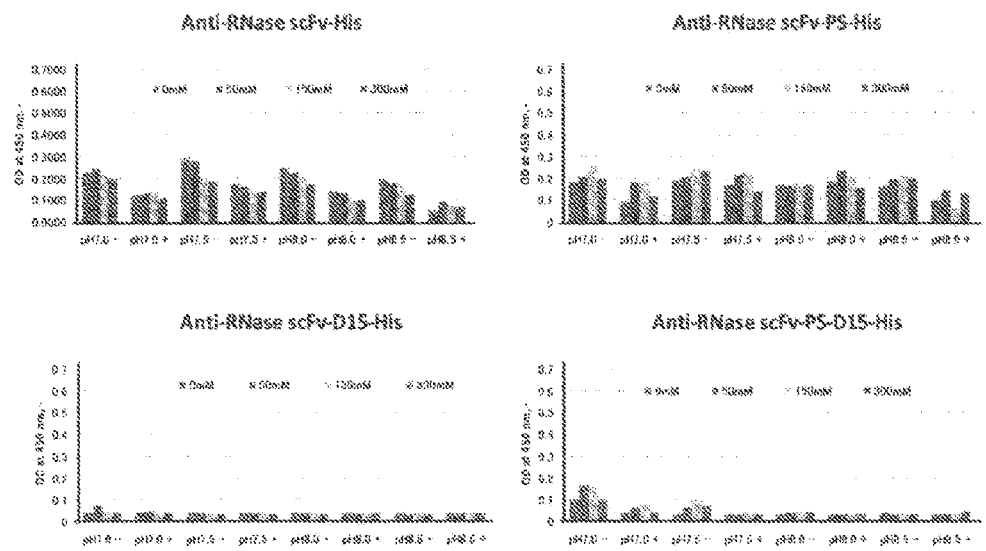
FIG. 9 is graphs showing the results of refolding of an antibody to which a low-isoelectric-point peptide and an affinity peptide are linked (PS).
Figure 10:
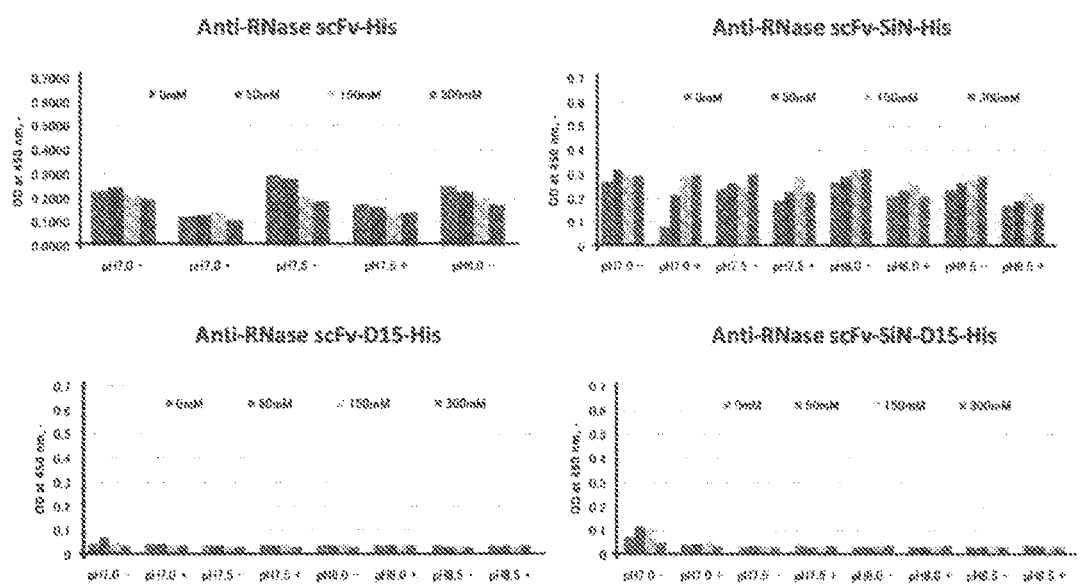
FIG. 10 is graphs showing the results of refolding of an antibody to which a low-isoelectric-point peptide and an affinity peptide are linked (SiN).

2. FIGS. 9 and 10 show the results.

FIG. 9 shows the results obtained when PS was used, and FIG. 10 shows the results obtained when SiN was used. As is clear from FIG. 9, the OD values of the inactive antibody binding to a peptide having an isoelectric point lower than the isoelectric point of the inactive antibody were small even in the presence of the affinity peptide PS, making it possible to improve the refolding efficiency of the antibody. As is also clear from FIG. 10, the refolding efficiency of the inactive antibody binding to a peptide having an isoelectric point lower than the isoelectric point of the inactive antibody was improved even in the presence of the affinity peptide SiN.

Test Example 8

Immobilization of Refolded Antibody on a Substrate

1. Using Example 2-1, Example 2-4, and Example 8-1, the refolded antibodies were brought into contact with a polymethyl methacrylate substrate to analyze whether these refolded antibodies were satisfactorily immobilized on the substrate via the peptide.

Specifically, Example 2-4, Example 8-1, and Comparative Example 4 above were each refolded as in Test Example 7 (liquid phase: 0.05 M TAPS Good's buffer, pH 8.5, NDSB201-free, NaCl concentration: 0 mM). Thereafter, each of the peptide-binding refolded antibodies was adjusted using PBS to a concentration of 50 ug/mL, and 100 uL each of the resulting product was added to a polymethyl methacrylate substrate (microplate) and incubated at 25° C. for 2 hours. Subsequently, the substrate was washed 5 times with PBST, and 300 uL each of PBST (2% BSA-PBST) containing 2% BSA was added and incubated at 25° C. for 1 hour. After the substrate was washed 5 times with PBST, biotin-labeled RNase was diluted in 2% BSA-PBST to 0 to 1 ug/mL, and 100 uL each thereof was added and incubated at 25° C. for 1 hour. Then, the substrate was washed 5 times with PBST, HRP-labeled streptavidin was diluted in 2% BSA-PBST to 0.2 ug/mL, and 100 uL each thereof was added and incubated at 25° C. for 1 hour. Then, the substrate was washed 5 times with PBST, and 100 uL each of TMB was added and incubated at 25° C. for 25 minutes; thereafter, 100 uL of 0.3M sulfuric acid was added to stop the coloring reaction (coloring reaction). Subsequently, the absorbance at 450 nm (sub wavelength at 650 nm) was measured using a microplate reader.

Further, a test was performed using Example 2-4 and Example 8-1, as in the manner described above, except that a hydrophilic polystyrene substrate (microplate) was used in place of the polymethyl methacrylate substrate (microplate), and the degree of immobilization on the hydrophilic polystyrene substrate was measured.

Figure 11:
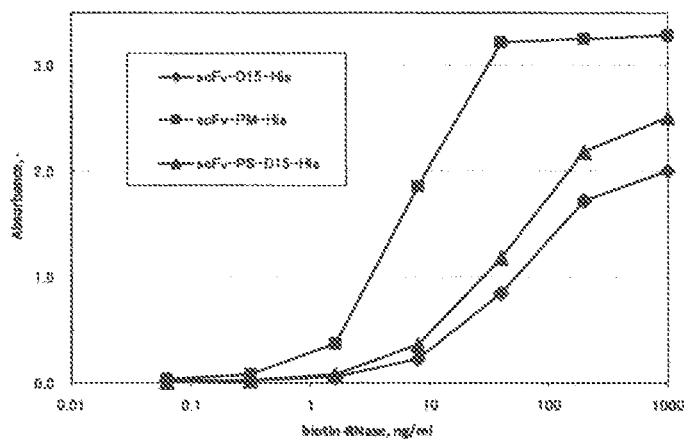
FIG. 11 is a graph showing the results obtained by immobilizing a refolded antibody on a substrate (PM).
Figure 12:
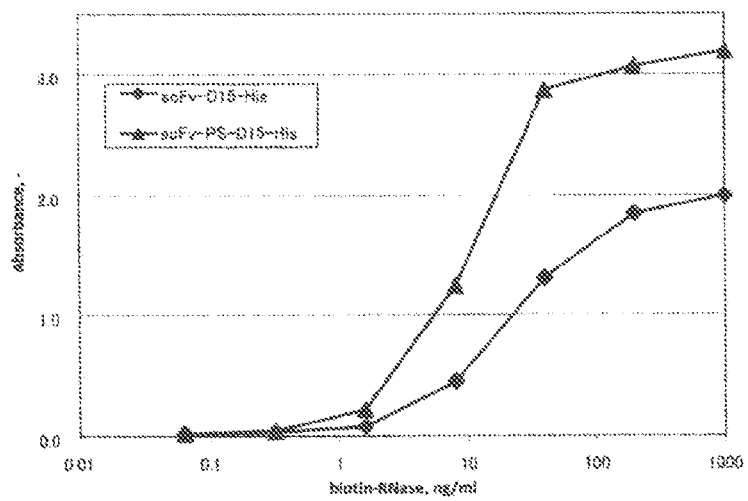
FIG. 12 is a graph showing the results obtained by immobilizing a refolded antibody on a substrate (PS).
Figure 13:
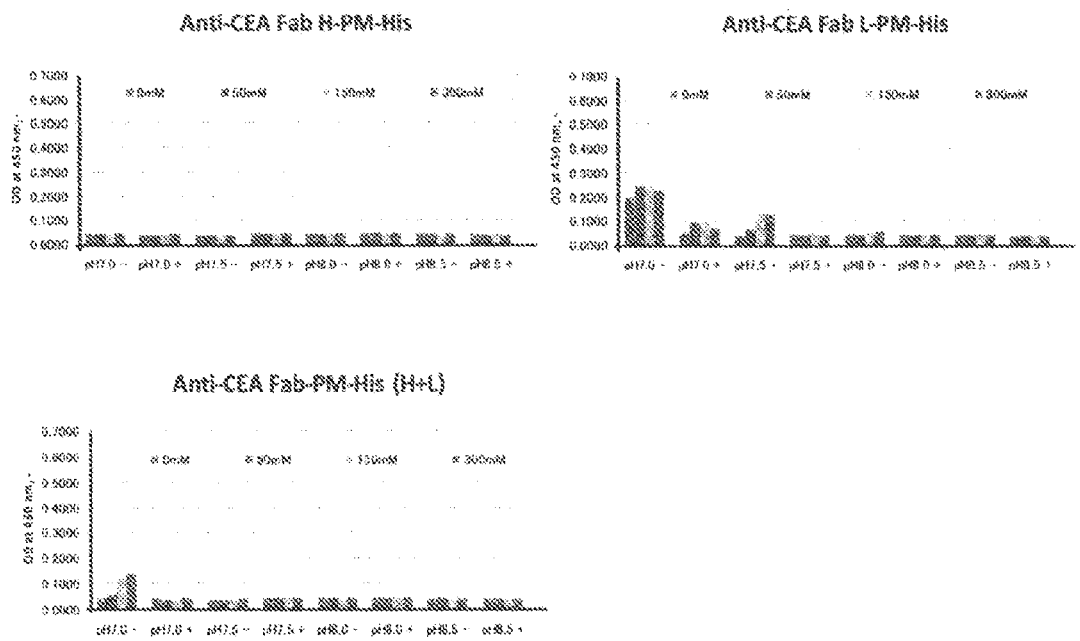
FIG. 13 is graphs showing the results of refolding of heavy-chain Fab and light-chain Fab (anti-CEA antibody).
Figure 14:
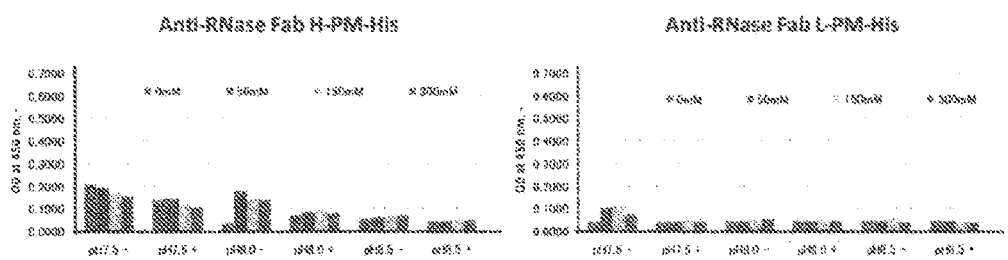
FIG. 14 is graphs showing the results of refolding of heavy-chain Fab and light-chain Fab (anti-RNase antibody).
Figure 15:
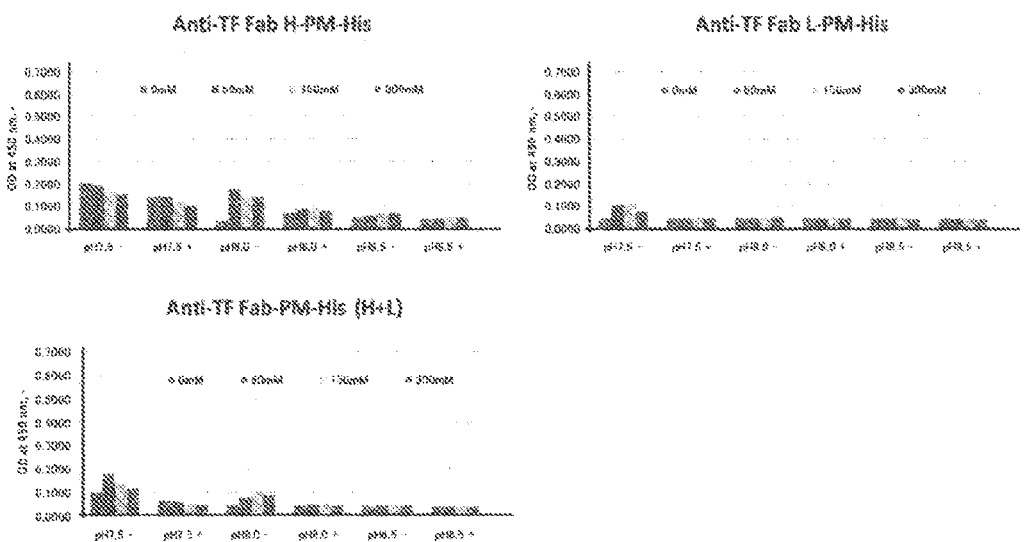
FIG. 15 is graphs showing the results of refolding of heavy-chain Fab and light-chain Fab (anti-TF189 antibody).
Figure 16:
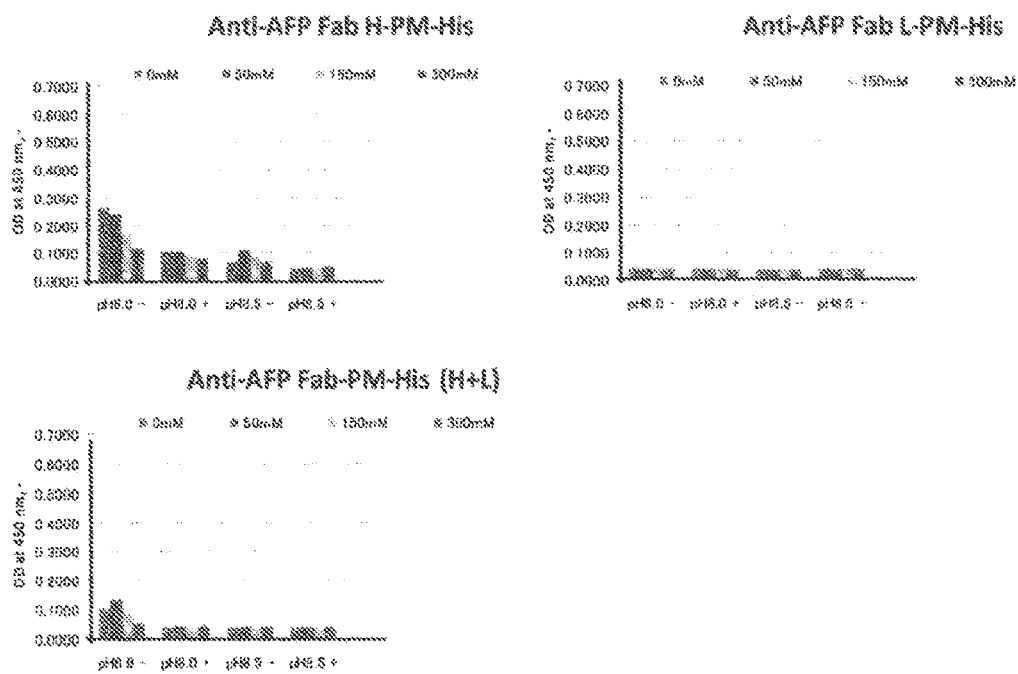
FIG. 16 is graphs showing the results of refolding of heavy-chain Fab and light-chain Fab (anti-AFP antibody).

2. FIGS. 11 and 12 show the results.

As is clear from FIG. 11, when the antibody of Example 2-1, to which the peptide (PM) having an affinity for polymethyl methacrylate and having an isoelectric point lower than the isoelectric point of the inactive antibody was introduced, was refolded, the refolded antibody was densely immobilized on the polymethyl methacrylate substrate due to the effect of PM, which was linked to the refolded antibody, giving a higher signal compared with other refolded antibodies to which a peptide having an affinity for polymethyl methacrylate was not linked.

The same tendency was also confirmed in FIG. 12. When the antibody of Example 8-1, to which both the peptide (PS) having an affinity for hydrophilic polystyrene and the peptide having an isoelectric point lower than the isoelectric point of the inactive antibody were introduced, was refolded, the refolded antibody was densely immobilized on a hydrophilic polystyrene substrate due to the effect of PS, which was linked to the refolded antibody, giving a higher signal, compared with other refolded antibodies to which the peptide having an affinity for hydrophilic polystyrene was not linked.

Test Example 9

Evaluation of Refolding Efficiency of Heavy-Chain Fab and Light-Chain Fab

1. Inactive antibodies binding to a peptide having an isoelectric point lower than the isoelectric point of the inactive antibodies were produced (Example 9-1 and Example 9-2 below) as in Test Example 1, except that a heavy-chain Fab antibody (Fab H) against CEA or a light-chain Fab antibody (Fab L) against CEA was used in place of the single-chain antibody of Example 1-1 (anti-CEA scFv-PM-His). Further, inactive antibodies binding to a peptide having an isoelectric point lower than the isoelectric point of the inactive antibodies were produced (Example 9-3 and Example 9-4 below) as in Test Example 2, except that a heavy-chain Fab antibody (Fab H) against RNase or a light-chain Fab antibody (Fab L) against RNase was used in place of the single-chain antibody of Example 2-1 (anti-RNase scFv-PM-His). Further, inactive antibodies binding to a peptide having an isoelectric point lower than the isoelectric point of the inactive antibodies were produced (Example 9-5 and Example 9-6 below) as in Test Example 4, except that a heavy-chain Fab antibody (Fab H) against TF189 or a light-chain-Fab antibody (Fab L) against TF189 was used in place of the single-chain antibody of Example 7 (anti-TF189 scFv-PM-His). Similarly, inactive antibodies binding to a peptide having an isoelectric point lower than the isoelectric point of the inactive antibodies were produced (Example 9-7 and Example 9-8 below) as in, for example, Example 9-1, except that AFP was used as an antibody.
Example 9-1: anti-CEA Fab H-PM-His (isoelectric point: 4.91)
Example 9-2: anti-CEA Fab L-PM-His (isoelectric point: 5.81)
Example 9-3: anti-RNase Fab H-PM-His (isoelectric point: 6.32)
Example 9-4: anti-RNase Fab L-PM-His (isoelectric point: 5.55)
Example 9-5: anti-TF189 Fab H-PM-His (isoelectric point: 6.54)
Example 9-6: anti-TF189 Fab L-PM-His (isoelectric point: 5.33)
Example 9-7: anti-AFP Fab H-PM-His (isoelectric point: 7.29)
Example 9-8: anti-AFP Fab L-PM-His (isoelectric point: 5.81)
The obtained peptide-binding inactive antibodies of Examples 9-1 to 9-8 were denatured and refolded as in Test Example 1 above to evaluate the refolding efficiency. In this test example, the denaturation and refolding were performed in the presence of each of the antibodies of Examples 9-1 to 9-8 alone, in the presence of a combination of Examples 9-1 and 9-2 (anti-CEA Fab-PM-His (H+L)), in the presence of a combination of Examples 9-3 and 9-4 (anti-RNase Fab-PM-His (H+L)), in the presence of a combination of Examples 9-5 and 9-6 (anti-TF189 Fab-PM-His (H+L)), or in the presence of a combination of Examples 9-7 and 9-8 (anti-AFP Fab-PM-His (H+L)).
2. FIGS. 13 to 16 show the results.
FIGS. 13 to 16 show the results with respect to CEA, RNase, TF189, and AFP, respectively. As is clear from these results, all of the OD values were small, which indicates that the refolding was efficiently performed.

Test Example 10

Calculation of Refolding Efficiency

In Test Example 9, the denaturation and refolding were performed as in Test Example 5, in the presence of a combination of Examples 9-1 and 9-2 (anti-CEA Fab-PM-His (H+L)), in the presence of a combination of Examples 9-3 and 9-4 (anti-RNase Fab-PM-His (H+L)), or in the presence of a combination of Examples 9-5 and 9-6 (anti-TF189 Fab-PM-His (H+L)) to calculate the refolding efficiency.
The results confirmed that the refolding efficiencies of anti-CEA Fab-PM-His (H+L), anti-RNase Fab-PM-His (H+L), and anti-TF189 Fab-PM-His (H+L) were 93%, 100%, and 100%, respectively, and were all high.

Test Example 11

Evaluation of Activity of Refolded Heavy-Chain Fab and Light-Chain Fab

1. Each of the refolded antibodies obtained by denatured and refolding the following peptide-binding inactive antibodies as in Test Example 10 was brought into contact with a polymethyl methacrylate substrate in accordance with the procedures described below, and the activity of each of the immobilized antibodies was evaluated. Further, anti-CEA Fab-PM-His (H+L), anti-RNase Fab-PM-His (H+L), and anti-TF189 Fab-PM-His (H+L) used in Test Example 10 were also subjected to refolding, brought into contact with a polymethyl methacrylate substrate, and the activity of each of the immobilized antibodies was evaluated. In the refolding, a liquid phase prepared by using 0.05 M TAPS Good's buffer and to have a pH of 8.5 with no addition of NDSB201 and have a NaCl concentration of 0 mM was used.
Antibodies against CEA
Example 1-1: anti-CEA scFv-PM-His
Example 9-1: anti-CEA Fab H-PM-His
Example 9-2: anti-CEA Fab L-PM-His
Antibodies against RNase
Example 2-1: anti-RNase scFv-PM-His
Example 9-3: anti-RNase Fab H-PM-His
Example 9-4: anti-RNase Fab L-PM-His
Antibodies against TF189
Example 7: anti-TF189 scFv-PM-His
Example 9-5: anti-TF189 Fab H-PM-His
Example 9-6: anti-TF189 Fab L-PM-His
More specifically, each of the thus-obtained refolded antibodies binding to a peptide having an isoelectric point lower than the isoelectric point of the inactive antibodies (anti-CEA antibodies, anti-RNase antibodies) was adjusted in PBS to a concentration of 100 ug/mL. Then, 100 uL each of the resulting product was added to a polymethyl methacrylate substrate (microplate) and incubated at 25° C. for 2 hours. Thereafter, the substrate was washed 5 times with PBST, and 300 uL each of PBST containing 2% BSA (2%

BSA-PBST) was added and incubated at 25° C. for 1 hour. Subsequently, the substrate was washed 5 times with PBST, biotin-labeled CEA or biotin-labeled PNase was diluted in 2% BSA-PBST to a concentration of 0 to 1 ug/mL, and 100 uL each of the resulting product was added and incubated at 25° C. for 1 hour. Then, after the substrate was washed 5 times with PBST, HRP-labeled streptavidin was diluted in 2% BSA-PBST to a concentration of 0.2 ug/mL, and 100 uL each thereof was added and incubated at 25° C. for 1 hour. Then, the substrate was washed 5 times with PBST, and 100 uL each of TMB was added and incubated at 25° C. for 15 minutes; thereafter, 100 uL of 0.3M sulfuric acid was added to stop the coloring reaction (coloring reaction). Subsequently, the absorbance at 450 nm (sub-wavelength at 650 nm) was measured using a microplate reader.

The refolded antibody binding to a peptide having an isoelectric point lower than the isoelectric point of the inactive antibody (anti-TF189 antibody) was adjusted in PBS as described above so that the concentration of the peptide-binding refolded antibody obtained as described above was 100 ug/mL. Then, 100 uL each of the resulting product was added to a polymethyl methacrylate substrate (microplate), and incubated at 25° C. for 2 hours. Thereafter, the substrate was washed 5 times with PBST, and 300 uL each of PBST containing 2% BSA (2% BSA-PBST) was added and incubated at 25° C. for 1 hour. Subsequently, the substrate was washed 5 times with PBST, transferrin was diluted in 2% BSA-PBST to a concentration of 0 to 1 ug/mL, and 100 uL each thereof was added and incubated at 25° C. for 1 hour. Then, after the substrate was washed 5 times with PBST, biotin-labeled anti-transferrin antibody was diluted in 2% BSA-PBST to 0.25 ug/mL, and 100 uL each thereof was added and incubated at 25° C. for 1 hour. Hereinafter, the same procedures described above were performed, and the absorbance was measured.

Figure 17:
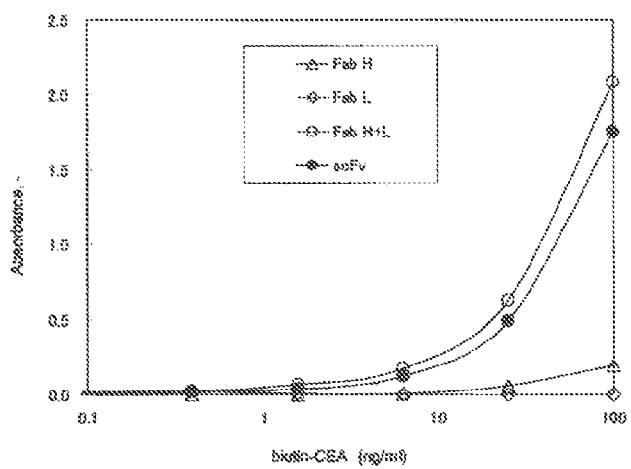
FIG. 17 is a graph showing the evaluation results of the activity of refolded heavy-chain Fab and light-chain Fab (anti-CEA antibody).
Figure 18:
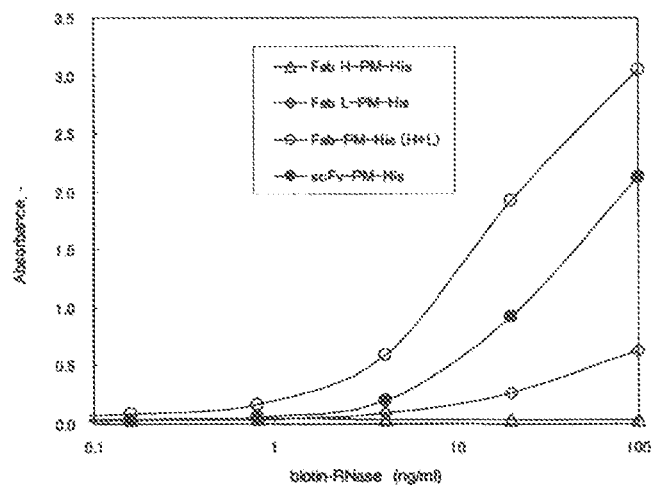
FIG. 18 is a graph showing the evaluation results of the activity of refolded heavy-chain Fab and light-chain Fab (anti-RNase antibody).
Figure 19:
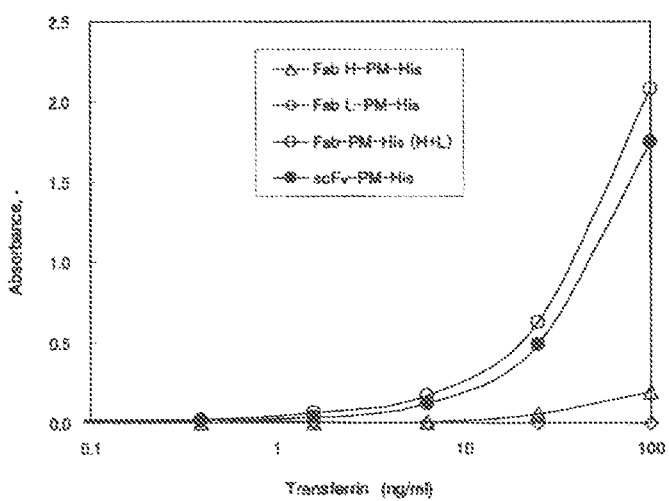
FIG. 19 is a graph showing the evaluation results of the activity of refolded heavy-chain Fab and light-chain Fab (anti-TF189 antibody).

2. FIGS. 17 to 19 show the results.

As is clear from FIGS. 17 to 19, when, in particular, Fab L and Fab H were combined, the desired activity was observed, as with the case where a single-chain antibody was used. Generally, H and L chains are considered to cooperatively perform antigen recognition. In this test example, a combined use of Fab L and Fab H in refolding achieved higher activity, compared with the case where Fab H or Fab L was used alone. This indicates that the present invention satisfactorily restored the desired activity originating from the antibody.

Test Example 12

Evaluation of Efficiency of Refolding of VHH

An inactive antibody binding to a peptide having an isoelectric point lower than the isoelectric point of the inactive antibody was prepared (Example 10 below) as in Example 1, except that camelid single domain VHH antibody was used as an antibody, and the test was performed as described above. For comparison, an antibody having the following structure, i.e., Comparative Example 6, was prepared, and the test was performed as described above.
Example 10: VHH-PM-His (isoelectric point: 6.05)
Comparative Example 6: VHH-His (isoelectric point: 8.20)

Figure 20:
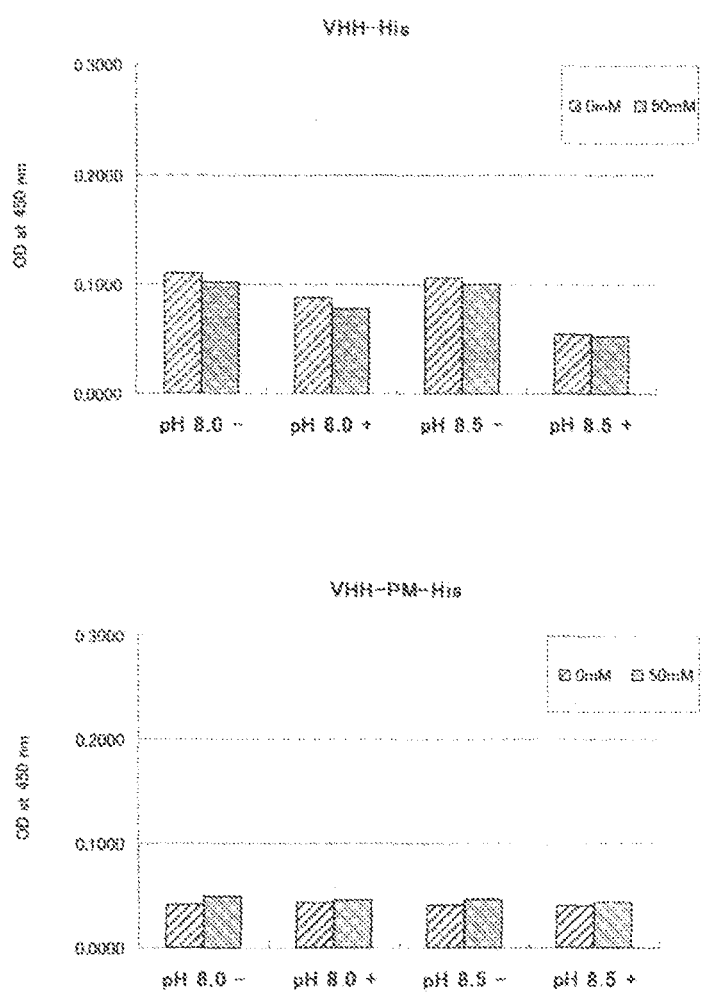
FIG. 20 is graphs showing the results of refolding of camelid single domain VHH antibody.

As shown in FIG. 20, even when a VHH single-domain antibody was used as an antibody, the aggregate was remarkably reduced by allowing the peptide to bind to the antibody. This indicates that it was possible to improve the refolding efficiency. The same tendency was observed even when the liquid phase had a lower pH, such as 7.5.

Test Example 13

Calculation of Refolding Efficiency

The denaturation and refolding of Example 10 and Comparative Example 6 of Test Example 12 were performed by dialysis as in Test Example 5, and the refolding efficiency was calculated. Specifically, Example 10 (VHH-PM-His) dissolved in 8 M Urea-PBS was diluted to obtain a solution of 0.5 mg/mL VHH-PM-His, 0.5 M urea, and 50 mM TAPS, and 1 mL of this solution was placed into a dialysis tube and dialyzed at 4° C. against an outer liquid, i.e., 1 L of 50 mM TAPS, overnight. Thereafter, the solution within the dialysis tube was collected, followed by centrifugation to remove the aggregate. The protein concentrations before and after the centrifugation were quantified by DC Protein Assay (produced by Bio-Rad Laboratories, Inc.), and the recovery was calculated. The recovery regarding Comparative Example 6 (VHH-His) was also calculated in a manner similar to the above.

The results confirmed that the recovery of Example 10 was 95%, while the recovery of Comparative Example 6 was 20%. In view of this, even when VHH was used as an antibody, inactive antibodies were effectively refolded.

Test Example 14

Calculation of Refolding Efficiency

The refolding efficiency of Example 10 was calculated using a method different from that used in Test Example 13. Specifically, the refolding efficiency was calculated from gel chromatography. First, two 5-mL Hi-Trap desalting gel filtration columns (produced by GE Healthcare) were connected to an ARTA Purifier UPC10 chromatography system (produced by GB Healthcare), and the columns were equilibrated with 50 mM TAPS (pH of 8.5). Next, Example 10 (VHH-PM-His) was dissolved in 8 M urea-PBS, which was diluted to 0.5 mg/mL VHH-PM-His, 0.5 M urea, 50 mM TAPS, and 0.5 M NDSB201. Then, 2 mL of the resulting solution was loaded onto the columns, and 50 M TAPS (pH of 8.5) was supplied. Subsequently, a solution containing the eluted protein in the first peak was recovered (recovery: 3 mL). The concentration of the recovered protein solution was quantified using DC protein assay (produced by Bio-Rad Laboratories, Inc.), and the recovery was calculated based on the applied amount and the recovery amount. The results confirmed that the recovery of Example 10 was 99%. This indicates that even when VHH was used as an antibody, the inactive antibody was efficiently refolded.

Test Example 15

Immobilization of Refolded VHH on a Substrate and Evaluation of the Activity

1. The refolded antibody of Example 10 was brought into contact with a polymethyl methacrylate substrate to analyze whether the antibody refolded was satisfactorily immobilized on the substrate via the peptide. Further, the immobilized antibody was also analyzed for whether it maintained the activity. The same analysis was also performed with respect to Comparative Example 6.

Specifically, after Example 10 was subjected to refolding in accordance with Test Example 13, the peptide-binding refolded antibody was adjusted in PBS to a concentration of 45 ug/mL, and 100 uL each of the resulting product was added to a polymethyl methacrylate substrate (microplate) and incubated at 25° C. for 2 hours. Thereafter, the substrate was washed 5 times with PBST, and 300 uL each of 2% BSA-PBST was added and incubated at 25° C. for 1 hour. Then, after the substrate was washed 5 times with PBST, biotin-labeled hCG was diluted in 2% BSA-PBST to 0 to 1 ug/mL, and 100 uL each thereof was added and incubated at 25° C. for 1 hour. Then, after the substrate was washed with PBST 5 times, HRP-labeled streptavidin was diluted in 2% BSA-PBST to 0.2 ug/mL, and 100 uL each thereof was added and incubated at 25° C. for 1 hour. Then, the substrate was washed 5 times with PBST, and 100 uL each of TMB was added and incubated at 25° C. for 15 minutes; thereafter, 100 uL of 0.3 M sulfuric acid was added to stop the coloring reaction (coloring reaction). Subsequently, the absorbance at 450 nm (sub-wavelength at 650 nm) was measured using a microplate reader.

Figure 21:
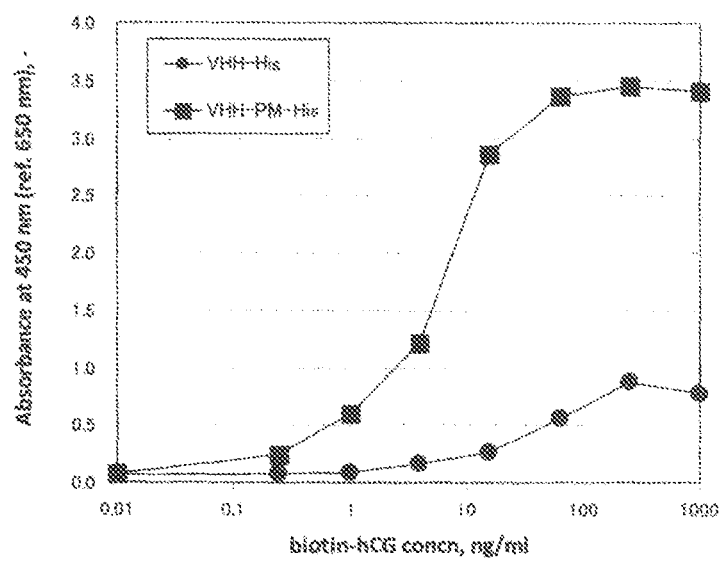
FIG. 21 is a graph showing the results obtained by immobilizing refolded VHH on a substrate and evaluation results of the activity thereof.

2. FIG. 21 shows the results.

As is clear from FIG. 21, when Example 10, to which the peptide (PM) having an affinity for polymethyl methacrylate and having an isoelectric point lower than the isoelectric point of the inactive antibody was introduced, was refolded, the refolded antibody was densely immobilized on the polymethyl methacrylate substrate due to the effect of PM, which was linked to the refolded antibody, giving a higher signal compared with other refolded antibodies to which a peptide having an affinity for polymethyl methacrylate was not linked. This indicates that in Example 10, the refolded antibody was densely immobilized on the substrate, and the desired activity originating from the antibody was satisfactorily restored.

The invention claimed is:

1. A method for improving the refolding efficiency of an antibody in a liquid phase, the method comprising the steps of:
   (A) denaturing an inactive antibody binding directly or indirectly through a linker to a peptide, wherein the peptide has an isoelectric point lower than the isoelectric point of the inactive antibody; and
   (B) dispersing the peptide-bound inactive antibody denatured in step (A) above in a buffer having a pH that is 1 to 4.5 units higher than the isoelectric point of the peptide-bound inactive antibody denatured in step (A) to obtain a refolded antibody,
   wherein a refolding efficiency of the refolded antibody is higher than a refolding efficiency obtained when the peptide represented by SEQ ID NO: 10 is bound to the inactive antibody, instead of the peptide of step (A) above, and
   wherein the peptide is selected from the amino acid sequence of any one of 5 (D5), 10 (D10) or 15(D15) aspartic acid residues, SEQ ID NOS: 1 to 4, or a variant of SEQ ID NOS: 1 to 4, wherein one to fifteen of the amino acids of SEQ ID NOS: 1 to 4 is (are) deleted or substituted with aspartic acid and/or glutamic acid residues and wherein the peptide has 4 to 20 more acidic amino acids than basic amino acids.

2. The refolding method according to claim 1, wherein the antibody is at least one member selected from the group consisting of single-chain antibodies, Fab fragments, F(ab')2 fragments, single-domain antibodies, multivalent single-chain antibodies, single-chain antibodies fused with a constant region, and full-length antibodies.

3. The refolding method according to claim 1, wherein the isoelectric point of the peptide is 8.5 or lower.

4. A process for producing a refolded antibody, the process comprising the steps of:
   improving the refolding efficiency of an antibody in a liquid phase comprising:
   (A) denaturing an inactive antibody binding directly or indirectly through a linker to a peptide, wherein the peptide has an isoelectric point lower than the isoelectric point of the inactive antibody; and
   (B) dispersing the peptide-bound inactive antibody denatured in step (A) above in a buffer having a pH that is 1 to 4.5 units higher than the isoelectric point of the peptide-bound inactive antibody denatured in step (A) to obtain a refolded antibody,
   wherein a refolding efficiency of the refolded antibody is higher than a refolding efficiency obtained when the peptide represented by SEQ ID NO: 10 is bound to the inactive antibody, instead of the peptide of step (A) above, and
   wherein the peptide is selected from the amino acid sequence of any one of 5 (D5), 10 (D10) or 15(D15) aspartic acid residues, SEQ ID NOS: 1 to 4, or a variant of SEQ ID NOS: 1 to 4, wherein one to fifteen of the amino acids of SEQ ID NOS: 1 to 4 is (are) deleted or substituted with aspartic acid and/or glutamic acid residues and wherein the peptide has 4 to 20 more acidic amino acids than basic amino acids.

5. The production process according to claim 4, wherein the antibody is at least one member selected from the group consisting of single-chain antibodies, Fab fragments, F(ab')2 fragments, single-domain antibodies, multivalent single-chain antibodies, single-chain antibodies fused with a constant region, and full-length antibodies.

6. The production process according to claim 4, wherein the isoelectric point of the peptide is 8.5 or lower.

7. The production process according to claim 4, wherein the linker is a peptide having an affinity for a substrate.

8. The refolding method according to claim 1, wherein the peptide is 5 to 10 amino acid residues in length.

9. The refolding method according to claim 1, wherein the amino acid residues of the peptide consist of aspartic acid residues, glutamic acid residues, or a combination thereof.

10. The production process according to claim 4, wherein the peptide is 5 to 10 amino acid residues in length.

11. The production process according to claim 4, wherein the amino acid residues of the peptide consist of aspartic acid residues, glutamic acid residues, or a combination thereof.

12. The refolding method according to claim 1, wherein the peptide is selected from SEQ ID NO: 4 or 5(D5), 10(D10) or 15(D15) aspartic acid residues.

13. The production process according to claim 4, wherein the peptide is selected from SEQ ID NO: 4 or 5(D5), 10(D10) or 15(D15) aspartic acid residues.

14. The refolding method according to claim 1, wherein the refolding efficiency is at least 88%.

15. The production process according to claim 4, wherein the refolding efficiency is at least 88%.

16. The refolding method according to claim 1, wherein the buffer is selected from the group consisting of
    a buffer comprising 50mM 2-(N-morpholino)ethanesulfonic acid at pH 6,
    a buffer comprising 50mM N-(2-acetamido)iminodiacetic acid at pH 6.5,
    a buffer comprising 50mM 3-(N-morpholino)propanesulfonic acid at pH 7,
    a buffer comprising 50 mM 2-[4-(2-Hydroxyethyl)-1-piperazinyl]ethanesulfonic acid at pH7.5,
    a buffer comprising 50mM N-(2-hydroxyethyl)piperazine-N'-3-propanesulfonic acid at pH 8, and
    a buffer comprising 50mM N-Tris(hydroxymethyl)methyl-3-aminopropanesulfonic acid at pH 8.5.

17. The production process according to claim 4, wherein the buffer is selected from the group consisting of
    a buffer comprising 50mM 2-(N-morpholino)ethanesulfonic acid at pH 6,
    a buffer comprising 50mM N-(2-acetamido)iminodiacetic acid at pH 6.5,
    a buffer comprising 50mM 3-(N-morpholino)propanesulfonic acid at pH 7,
    a buffer comprising 50 mM 2-[4-(2-Hydroxyethyl)-1-piperazinyl]ethanesulfonic acid at pH7.5,
    a buffer comprising 50 mM N-(2-hydroxyethyl)piperazine-N'-3-propanesulfonic acid at pH 8, and
    a buffer comprising 50mM N-Tris(hydroxymethyl)methyl-3-aminopropanesulfonic acid at pH 8.5.

* * * * *